(12) United States Patent
Martin

(10) Patent No.: US 8,119,771 B2
(45) Date of Patent: Feb. 21, 2012

(54) PRODUCTS FOR ALTERING IL-33 ACTIVITY AND METHODS THEREOF

(75) Inventor: Seamus J. Martin, County Kildare (IE)

(73) Assignee: The Provost, Fellow and Scholars of the College of the Holy and Undivided Trinity of Queen Elizabeth, Near Dublin, Dublin (IE)

( * ) Notice: Subject to any disclaimer, the term of this patent is extended or adjusted under 35 U.S.C. 154(b) by 224 days.

(21) Appl. No.: 12/451,053

(22) PCT Filed: Apr. 28, 2008

(86) PCT No.: PCT/IE2008/000050
§ 371 (c)(1),
(2), (4) Date: Oct. 23, 2009

(87) PCT Pub. No.: WO2008/132709
PCT Pub. Date: Nov. 6, 2008

(65) Prior Publication Data
US 2010/0260705 A1    Oct. 14, 2010

(30) Foreign Application Priority Data
Apr. 26, 2007  (IE) .................................. 2007/0312

(51) Int. Cl.
*C07K 14/54* (2006.01)

(52) U.S. Cl. ..................................... 530/351; 435/69.52
(58) Field of Classification Search .................. None
See application file for complete search history.

(56) References Cited

FOREIGN PATENT DOCUMENTS
| | | |
|---|---|---|
| WO | WO 2004/056868 | 7/2004 |
| WO | WO 2005/079844 | 9/2005 |
| WO | WO 2007/130627 | 11/2007 |

OTHER PUBLICATIONS
International Search Report dated Sep. 10, 2009.

*Primary Examiner* — Prema Mertz
(74) *Attorney, Agent, or Firm* — Jacobson Holman PLLC

(57) ABSTRACT

Products for altering IL-33 activity including antibodies that specifically bind to an epitope with the polypeptide sequence of IL-33 such as antibodies that specifically bind to a protease cleavage region of IL-33 comprising the amino acid sequence of SEQ ID No. 17, or SEQ ID NO. 16, or SEQ ID NO. 10; isolated IL-33 polypeptide(s); and compositions comprising a soluble IL-33 receptor linked to an enzyme capable of cleaving IL-33 or an antibody that binds to IL-33 linked to an enzyme capable of cleaving IL-33. The invention also relates to methods of altering IL-33 activity using the products described herein.

6 Claims, 23 Drawing Sheets

PRODUCTS FOR ALTERING IL-33 ACTIVITY AND METHODS THEREOF

This is a national stage of PCT/IE08/000,050 filed Apr. 28, 2008 and published in English, which has a priority of Irish no. 2007/0312 filed Apr. 26, 2007, hereby incorporated by reference.

INTRODUCTION

This invention relates to products for altering the activity of IL-33 and methods therefore.

Caspases (cysteine aspartic acid-specific proteases) are highly specific proteases that have been implicated in apoptosis and inflammation (Creagh et al., 2003; Martinon and Tschopp, 2004). The inflammatory caspases (caspases-1, -4, -5) are activated in response to pathogen products such as lipopolysaccharide (LPS) that engage members of the Toll-like receptor (TLR) family (Thornberry et al., 1992; Martinon and Tschopp, 2004). Previous studies have firmly established that caspase-1 plays a critical role in the innate immune response to infectious agents through proteolytic processing of pro-IL-1β and pro-IL-18 to their mature forms (Li et al., 1995; Kuida et al., 1995; Ghayur et al., 1997; Gu et al., 1997).

Recently, caspase-1 has also been implicated in the proteolytic maturation of the novel IL-1 family cytokine, IL-33/IL-1F11 (Schmitz et al., 2005). IL-33 is a ligand for the IL-1R family member ST2/T1 (Schmitz et al., 2005), which has previously been linked with maturation of $T_H2$ cells and negative regulation of IL-1R and TLR4 signalling (Brint et al., 2004; Meisel et al., 2001; Xu et al., 1998). Antagonistic antibodies against ST2 or IgG-ST2 fusion proteins lead to enhancement of $T_H1$ responses and attenuation of $T_H2$-associated effects (Lohning et al., 1998; Xu et al., 1998). Furthermore, in a pulmonary granuloma model induced with *Schistosoma mansoni* eggs, the production of $T_H2$ cytokines was severely impaired in ST2-deficient mice (Townsend et al., 2000).

Although relatively little is currently known concerning the factors that stimulate IL-33 production and secretion, an artificially-truncated form of this cytokine was said to enhance production of $T_H2$ cytokines from in vitro polarized $T_H2$ cells and to suppress $T_H1$ cytokine production (Schmitz et al., 2005). Administration of the same truncated form of IL-33 in vivo induced expression of IL-4, IL-5 and IL-13 and also led to eosinophilia, splenomegaly and increased levels of serum IgE and IgA (Schmitz et al., 2005; Chackerian et al., 2007). IL-33 is also a potent activator of mast cells and can promote in vitro maturation of these cells from bone marrow precursors (Allakhverdi et al., 2007; Ali et al., 2007). Collectively, these data suggest that IL-33 is instrumental in reinforcing $T_H2$ responses, by acting as a ligand for the ST2 receptor.

However, the role of caspase-1, or other inflammatory caspases, in the maturation of IL-33 remains enigmatic. High concentrations of recombinant caspase-1 have been reported to promote proteolysis of IL-33 in vitro and this has been proposed as a mechanism of activation of this cytokine, similar to IL-1β (Schmitz et al., 2005).

STATEMENTS OF INVENTION

We have surprisingly discovered that IL-33 is active as a full-length cytokine, and does not require proteolytic maturation by caspases for production of the biologically active cytokine. Furthermore, we have found that proteolysis of IL-33 is not necessary for ST2 receptor binding or ST2-dependent NFκB activation. We have also demonstrated that IL-33 is efficiently cleaved at a conserved motif by caspases to produce two IL-33 fragments. Caspase cleavage of IL-33 renders IL-33 susceptible to protease-mediated degradation and attenuates the biological activity of IL-33. We have shown that IL-33 is processed by caspases activated during apoptosis (for example caspases-3 and -7) but is not a physiological substrate for the inflammatory caspases (for example caspase-1, -4 and -5). Consistent with this, we have also shown that IL-33 was processed, at the cleavage motif we have identified, within apoptotic but not necrotic cells. Thus, contrary to the previous proposal that caspases activate IL-33 (Schmitz et al., 2005), we have surprisingly found that caspase-mediated proteolysis acts to dampen the pro-inflammatory properties of this cytokine.

Our data suggest that IL-33 does not require proteolysis for activation, but rather, that IL-33 stability and bioactivity are diminished through caspase-dependent proteolysis within apoptotic cells. Thus, caspase-mediated proteolysis acts as a switch to dampen the pro inflammatory properties of IL-33.

We believe that the surprising finding of a specific proteolytic cleavage site with the IL-33 polypeptide is highly important as this proteolytic cleavage site may be the key mechanism of controlling IL-33 activity. The proteolytic cleavage site that we have identified can be used as a target for attenuating the biological activity of IL-33 both in vitro and in vivo. In addition, the identification of the specific target can be used in the diagnostics, prophylaxis and treatment aspects of conditions, diseases and disorders associated with IL-33 activity.

In one aspect, the invention provides an antibody to alter the activity of IL-33, the antibody specifically binding to a peptide comprising the amino acid sequence of SEQ ID NO. 16. The antibody may specifically bind to an epitope comprising the amino acid sequence of SEQ ID No. 17 or an epitope comprising the tetrapeptide sequence of SEQ ID NO. 10. The antibody may be a polyclonal antibody, alternatively, the antibody may be a monoclonal antibody.

The binding of the antibody may attenuate IL-33 activity. The binding of the antibody may inhibit IL-33 activity. The binding of the antibody may prevent IL-33 activating the ST2 receptor. Alternatively, the binding of the antibody may promote proteolysis of IL-33, for example the antibody may be a catalytic antibody.

In a further aspect, the invention also provides an antibody to alter the activity of ST2 bound IL-33 (IL-33-ST2), the antibody specifically binding to an epitope within the polypeptide sequence of SEQ ID NO. 2. The antibody may be a neutralising antibody. The binding of the antibody to IL-33 may prevent the ST2 receptor from interacting with and/or associating with a co-receptor of the ST2-IL-33 receptor. For example, the binding of the antibody to IL-33 may prevent the ST2 receptor from interacting with and/or associating with IL-1 accessory protein. Alternatively, the binding of the antibody may prevent IL-33 from activating the ST2 receptor. The antibody may be a polyclonal antibody. Alternatively, the antibody may be a monoclonal antibody.

The invention further provides an immunogenic composition comprising an antibody as described herein linked to an enzyme capable of cleaving IL-33.

The enzyme may be a protease. For example, the protease may be a caspase such as a caspase selected from any one of caspase-1, caspase-2, caspase-3, caspase-4, caspase-5, caspase-6, caspase-7, caspase-8, caspase-9, caspase-10 and caspase-14. The caspase may be selected from caspase-3 or caspase-7. Alternatively, the protease may be trypsin or thrombin, or any other common protease.

The enzyme may be chemically linked to the antibody. The enzyme may be chemically linked to the antibody through a succinimidyl-4-(maleimidomethyl)cyclohexane-1-carboxylate crosslinker.

The invention also provides for a composition comprising a soluble IL-33 receptor linked to an enzyme capable of cleaving IL-33.

The soluble IL-33 receptor may be ST2/T1. The soluble IL-33 receptor may be a recombinant protein.

The composition may further comprise an Fc coding portion of an immunoglobulin. The soluble receptor may be linked to the Fc coding portion. The composition may comprise an ST2/T1-Fc fusion protein.

The enzyme may be a protease. For example, the protease may be a caspase such as a caspase selected from any one of caspase-1, caspase-2, caspase-3, caspase-4, caspase-5, caspase-6, caspase-7, caspase-8, caspase-9, caspase-10 and caspase-14.

The caspase may be selected from caspase-3 or caspase-7. Alternatively, the protease may be trypsin or thrombin or any other common protease.

The invention also provides for use of an antibody, or an immunogenic composition, or a composition all of which are described herein in the treatment of a disease associated with IL-33 pro-inflammatory activity. For example the disease may be one or more of asthma, Rheumatoid arthritis, Chronic Obstructive Pulmonary Disease (COPD), sepsis, Crohns disease, colitis, psoriasis and inflammatory bowel disorder (IBD).

The invention further provides for a method for the prophylaxis and/or treatment of a disease associated with IL-33 pro-inflammatory activity comprising the step of administering an effective amount of an antibody, or an immunogenic composition, or a composition of the kind described herein to a subject. The disease may be one or more of asthma, Rheumatoid arthritis, and Chronic Obstructive Pulmonary Disease (COPD), sepsis, Crohns disease, colitis, psoriasis and inflammatory bowel disorder (IBD).

In a different aspect, the invention provides for a method for inhibiting the biological activity of IL-33 comprising the step of introducing a purified caspase into an IL-33 producing cell wherein the purified caspase is capable of cleaving IL-33. The caspase may be selected from any one of caspase-1, caspase-2, caspase-3, caspase-4, caspase-5, caspase-6, caspase-7, caspase-8, caspase-9, caspase-10 and caspase-14. The caspase may be caspase-3 or caspase-7. The caspase may be a recombinant caspase. The caspase may be introduced into a cell through a gene delivery vector. The gene delivery vector may have been engineered in vitro to express the caspase gene.

The invention further provides for the use of an antibody that specifically binds to a caspase cleaved form of IL-33 to monitor apoptosis in IL-33 producing cells and/or tumours. The antibody may specifically bind to an epitope within the amino acid sequence of SEQ ID NO. 12 or SEQ ID NO. 13.

In another aspect, the invention provides for an isolated IL-33 polypeptide that is resistant to caspase mediated cleavage. The IL-33 polypeptide may have been modified in vitro to make it resistant to caspase cleavage. For example, the caspase cleavage site may have been mutated. The isolated IL-33 polypeptide may comprise the sequence of SEQ ID NO. 4.

The invention also provides for the use of an isolated IL-33 polypeptide that is resistant to caspase mediated cleavage as described herein, in the treatment of a disease associated with down regulated IL-33 activity and/or an excessive $T_H1$ response. The invention also provides for the use of an isolated full length IL-33 polypeptide comprising the amino acid sequence of SEQ ID NO. 2 in the treatment of a disease associated with down regulated IL-33 activity and/or an excessive $T_H1$ response. The disease may be one or both of cancer and an infectious disease such as a viral infection. The disease may be a cardiac disease associated with down regulated IL-33 activity and/or an excessive $T_H1$ response.

The invention further provides for a method for the prophylaxis and/or treatment of a disease associated with down regulated IL-33 activity and/or an excessive $T_H1$ response comprising the step of administering an effective amount of an isolated IL-33 polypeptide that is resistant to caspase mediated cleavage as described herein to a subject. The invention also provides for a method for the prophylaxis and/or treatment of a disease associated with down regulated IL-33 activity and/or an excessive $T_H1$ response comprising the step of administering an effective amount of an isolated full length IL-33 polypeptide comprising the amino acid sequence of SEQ ID NO. 2 to a subject. The disease may be one or both of cancer and an infectious disease such as a viral infection. The disease may be a cardiac disease associated with down regulated IL-33 activity and/or an excessive $T_H1$ response.

The invention also provides for an in vitro method for identifying compounds and/or molecules suitable for modifying the biological activity of IL-33 comprising the steps of:
   (a) contacting an IL-33 polypeptide with a compound and/or a molecule to be tested;
   (b) assaying the activity of IL-33 in the presence of said compound and/or molecule; and
   (c) comparing the level of IL-33 activity from step (b) to the level of IL-33 activity in the absence of said compound and/or molecule.

The compound and/or molecule identified may bind to IL-33. The compound and/or molecule identified may bind to IL-33 in the caspase cleavage region. For example, the compound and/or molecule identified may bind to any one of the amino acid sequences of SEQ ID NO. 10, SEQ ID NO. 16 and SEQ ID NO. 17.

The compounds and/or molecules identified may neutralise the activity of IL-33. The compound and/or molecule identified inhibit the activity of IL-33. For example, the compound and/or molecule identified may cleave IL-33.

The compound and/or molecule identified may be used in the treatment of a disease associated with IL-33 pro-inflammatory activity. The disease is one or more of asthma, Rheumatoid arthritis, and Chronic Obstructive Pulmonary Disease (COPD), sepsis, Crohns disease, colitis, psoriasis and inflammatory bowel disorder (IBD).

The invention further provides for a method for the prophylaxis and/or treatment of a disease associated with IL-33 pro-inflammatory activity comprising the step of administering an effective amount of a compound and/or molecule identified by the method described herein to a subject. The disease may be one or more of asthma, Rheumatoid arthritis, and Chronic Obstructive Pulmonary Disease (COPD), sepsis, Crohns disease, colitis, psoriasis and inflammatory bowel disorder (IBD).

BRIEF DESCRIPTION OF THE DRAWINGS

The invention will be more clearly understood from the following description of embodiments thereof, given by way of example only, with reference to the accompanying drawings, in which:—

Figure 2:
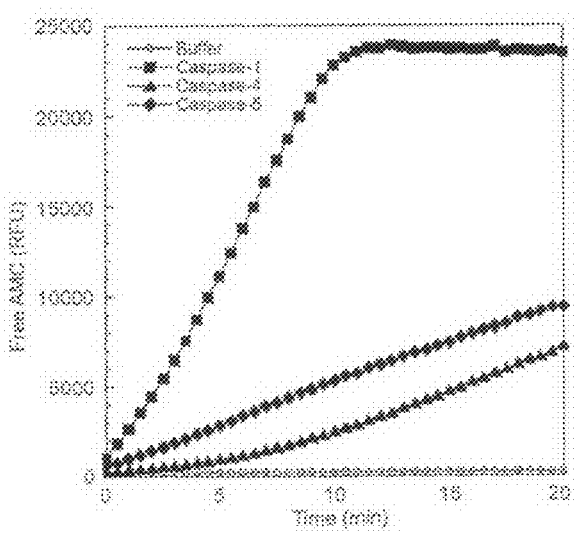
Figure 3:
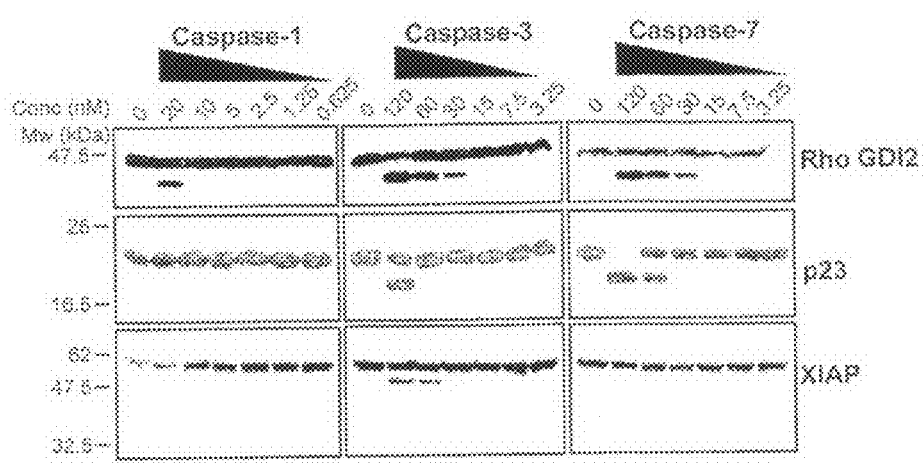
Figure 4:
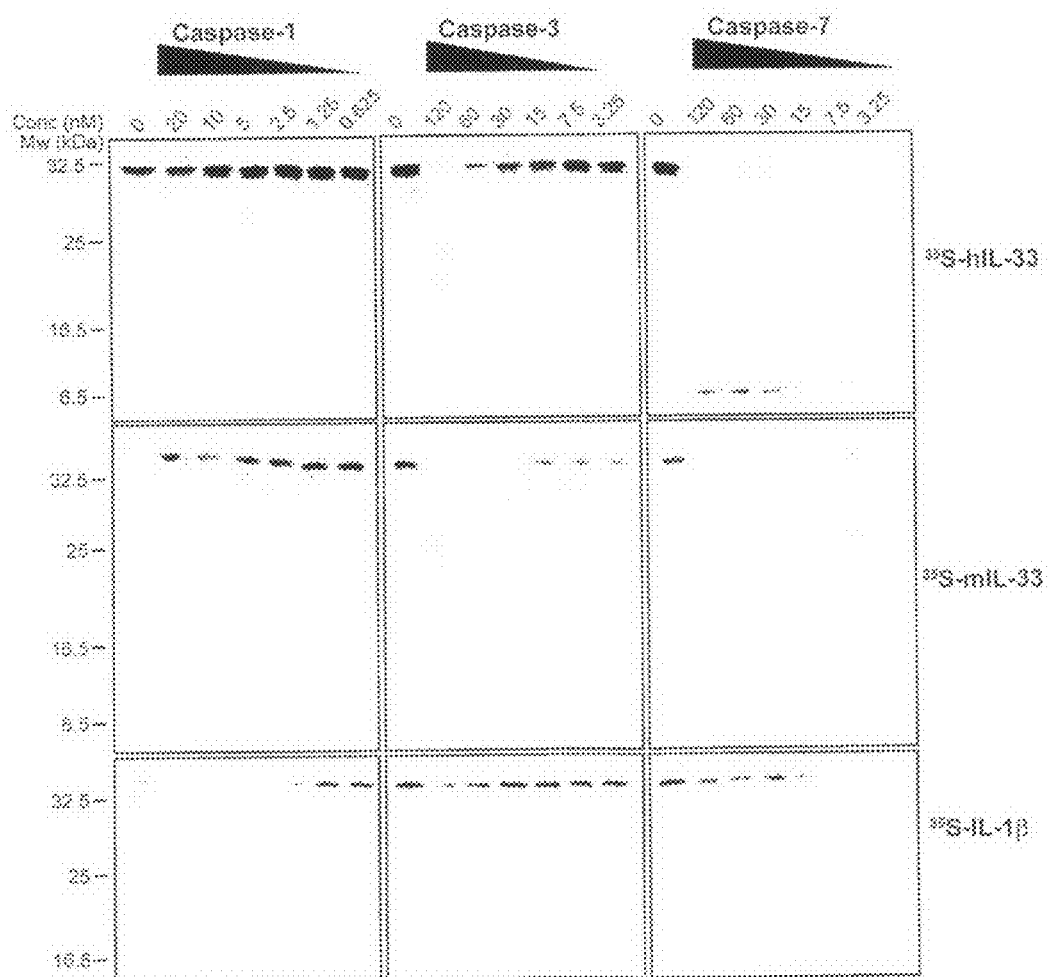
Figure 5:
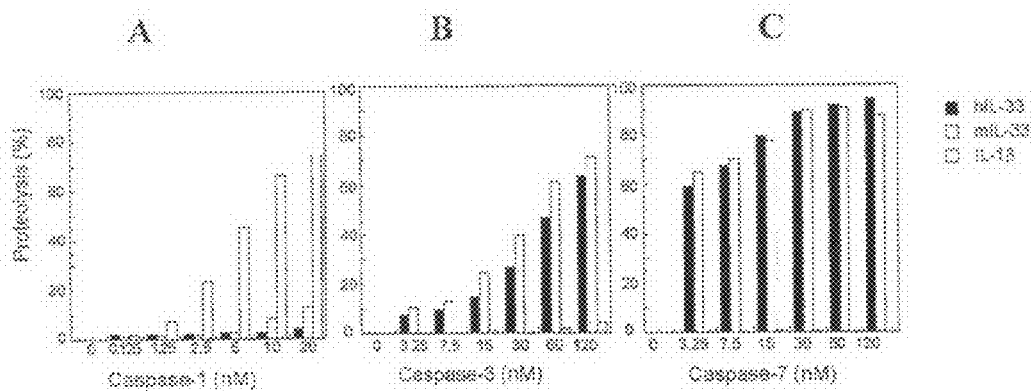
Figure 6:
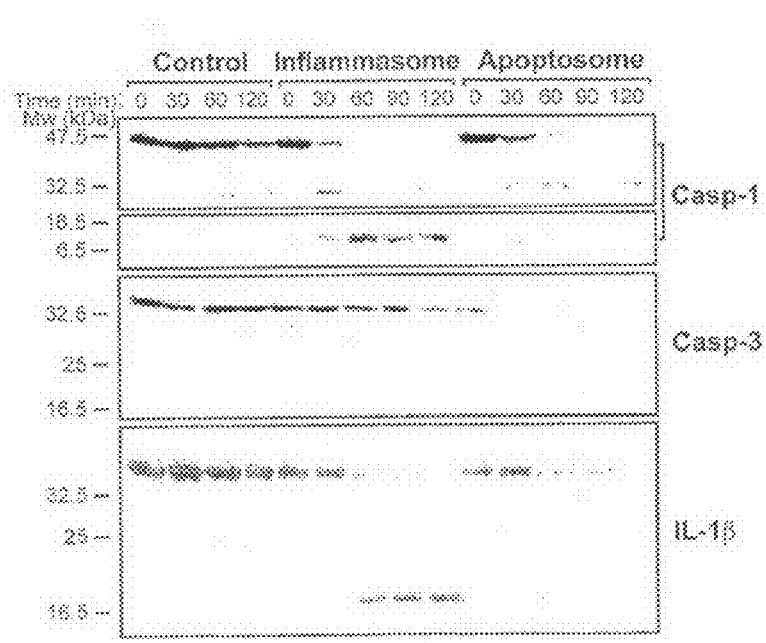
Figure 7:
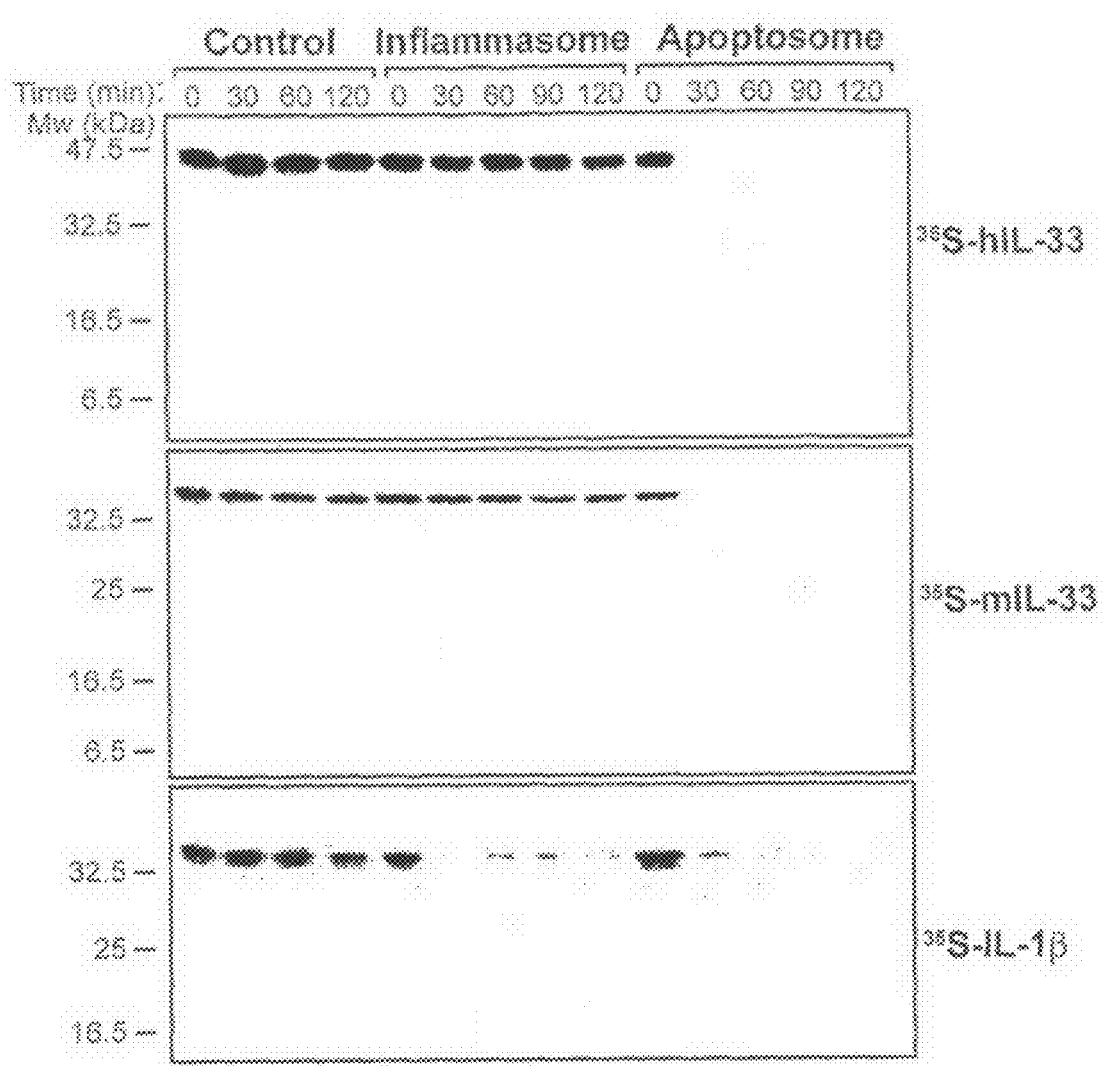
Figure 8:
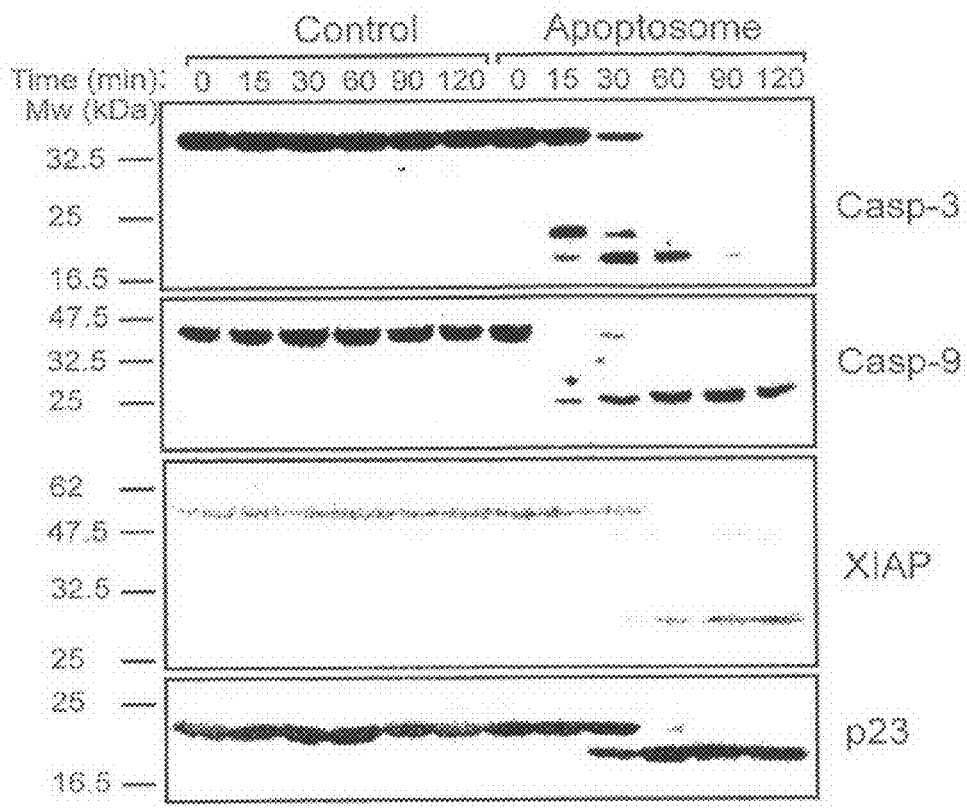
Figure 9:
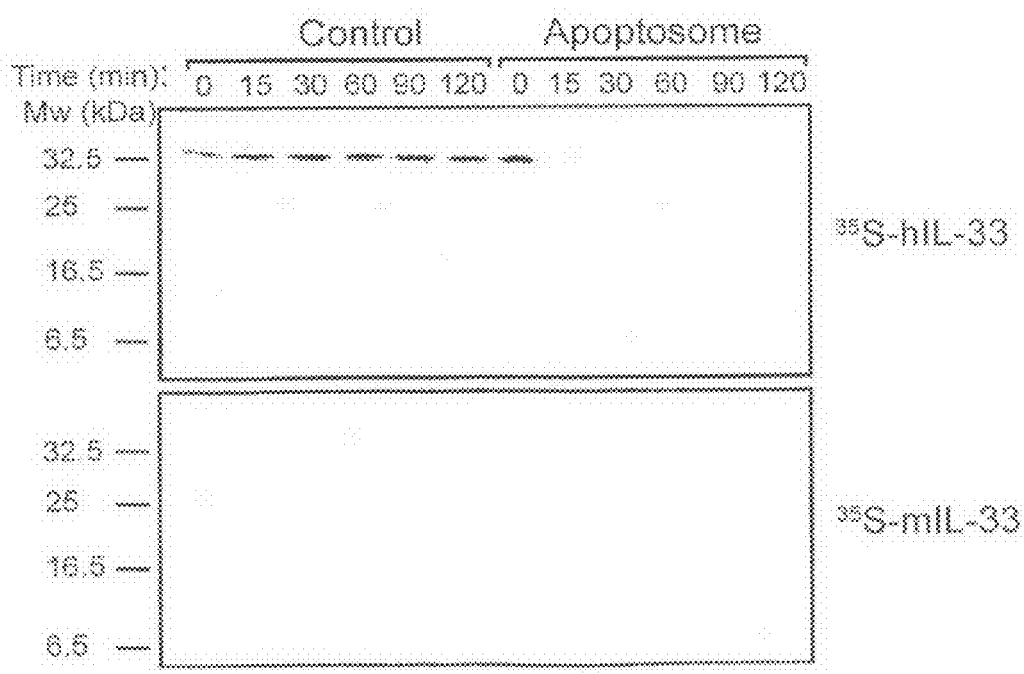
Figure 10:
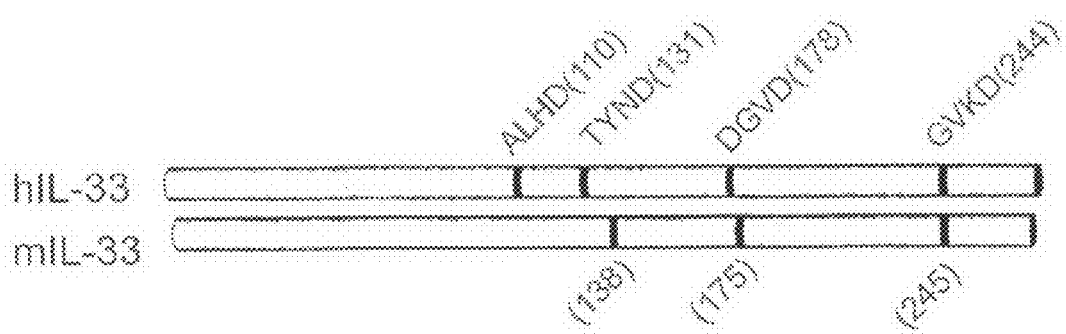
Figure 11:
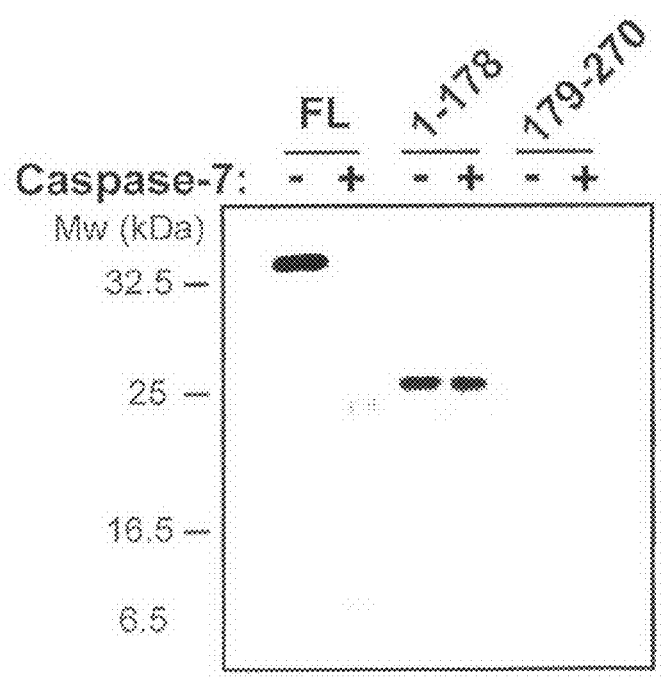
Figure 12:
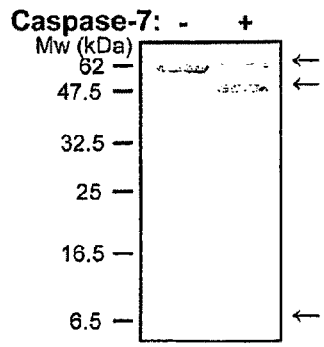
Figure 13:
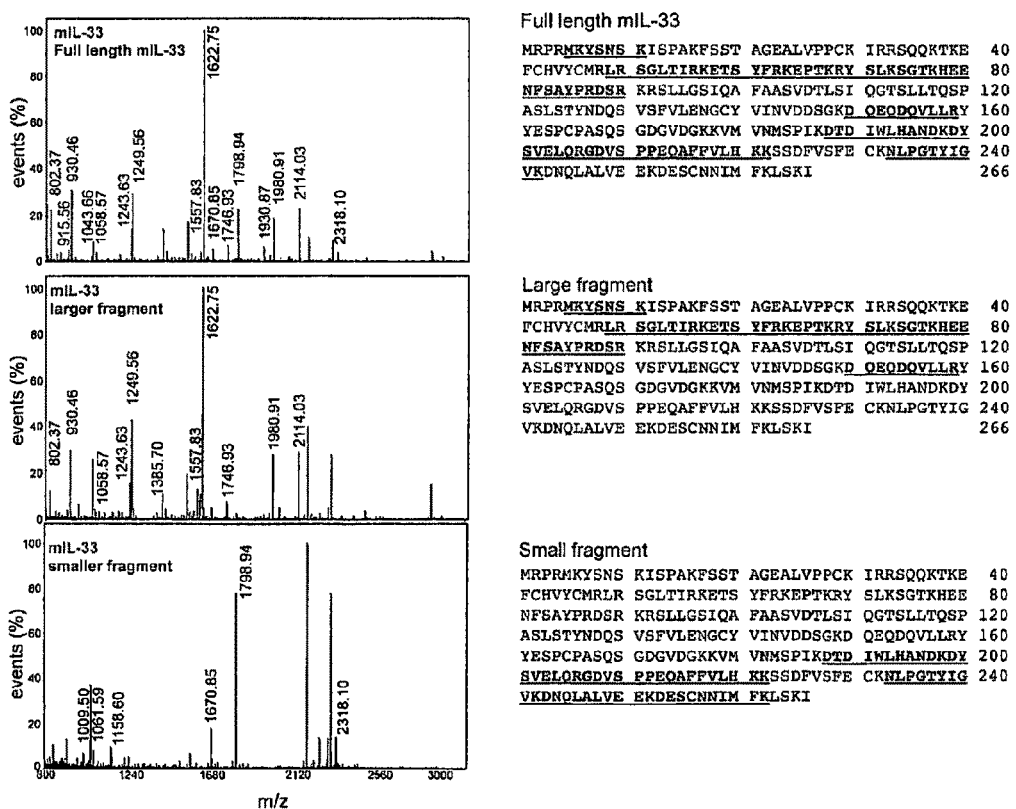
Figure 14:
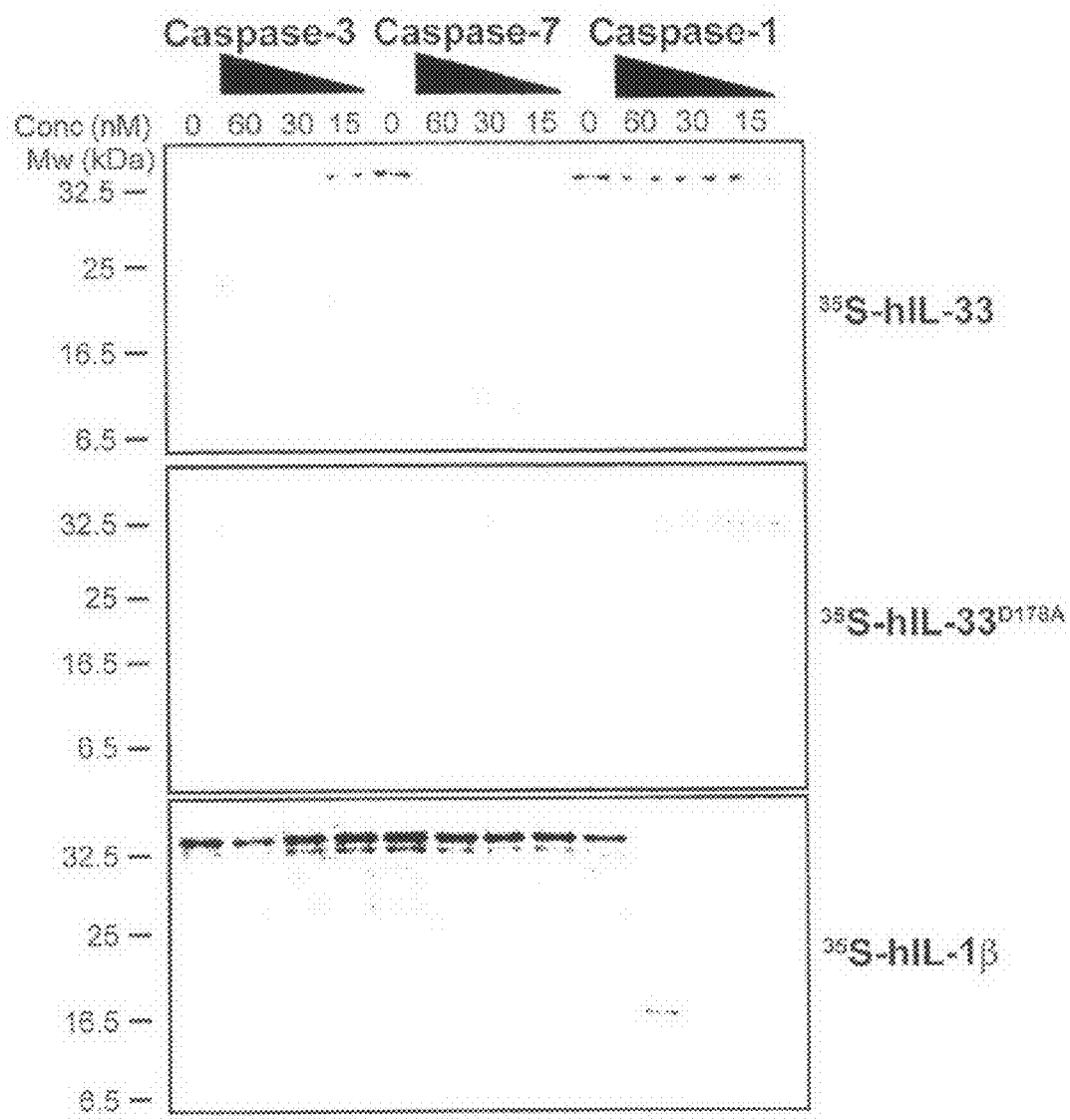
Figure 15:
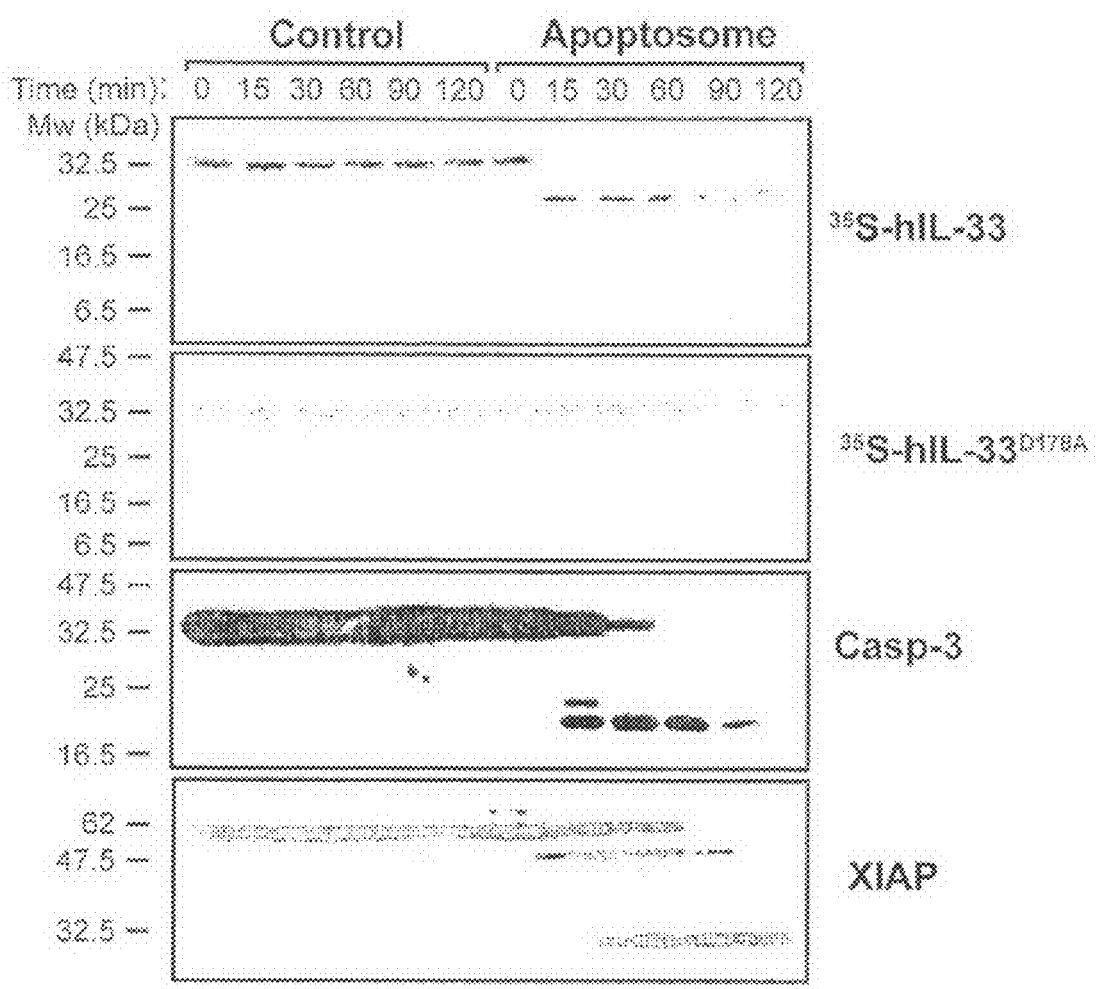
Figure 16:
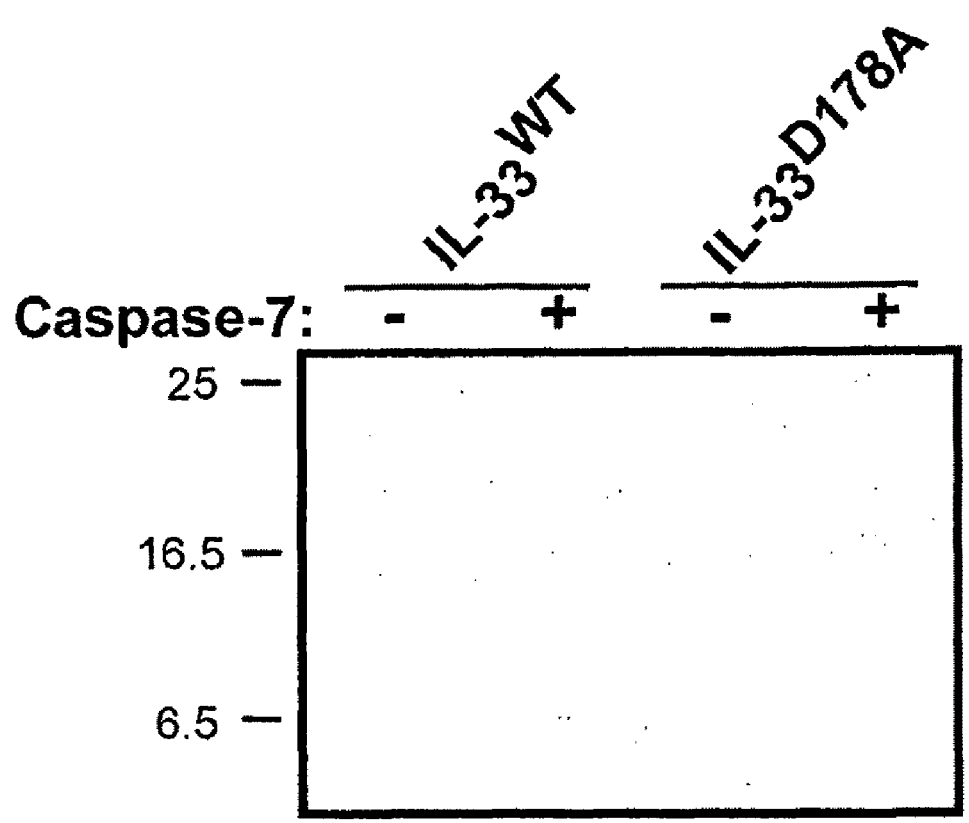
Figure 17:
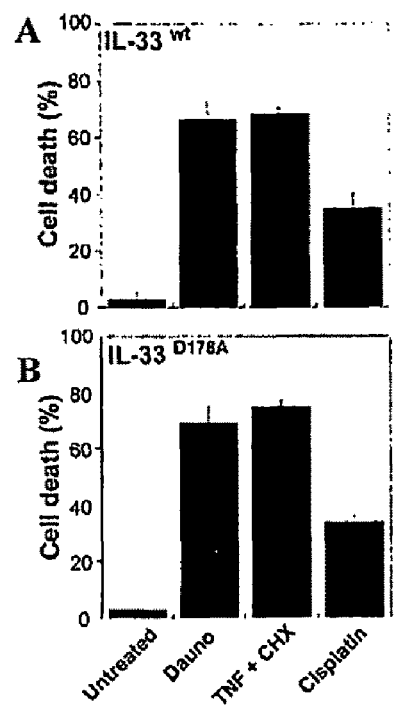
Figure 18:
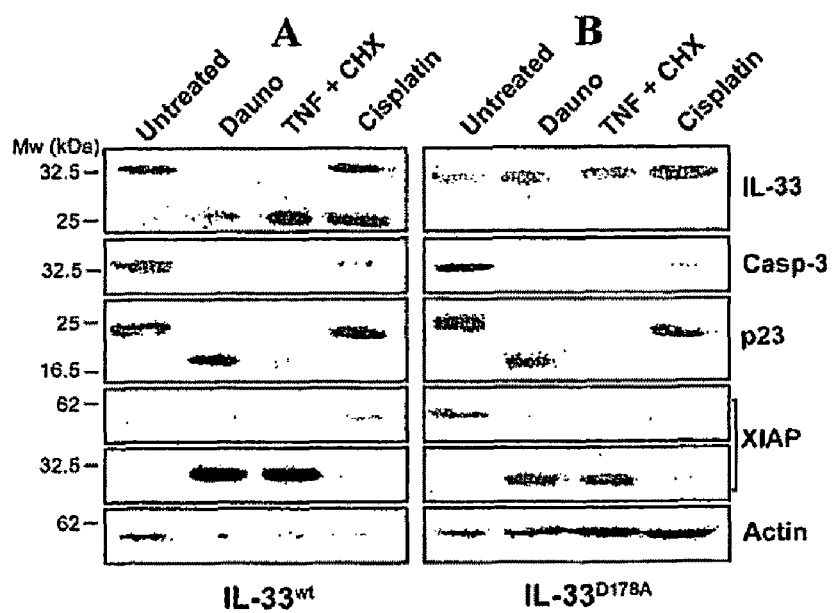
Figure 19:
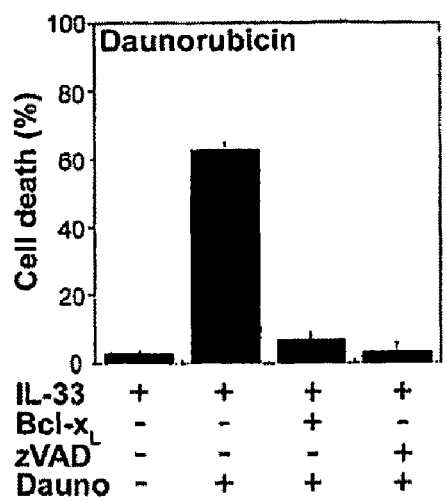
Figure 20:
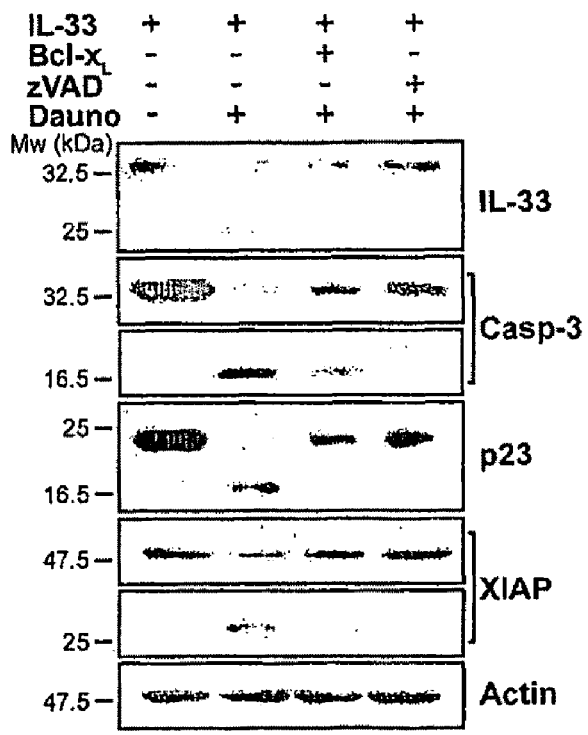
Figure 21:
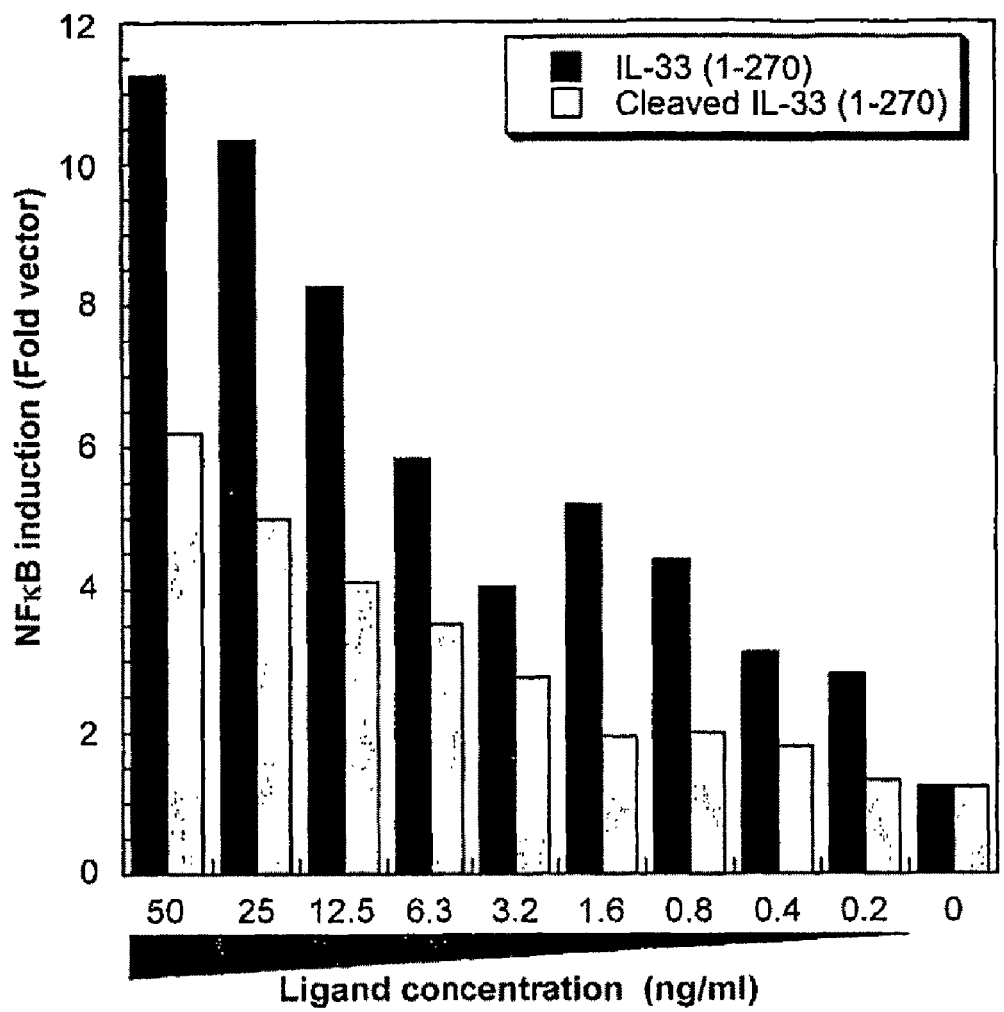
Figure 22:
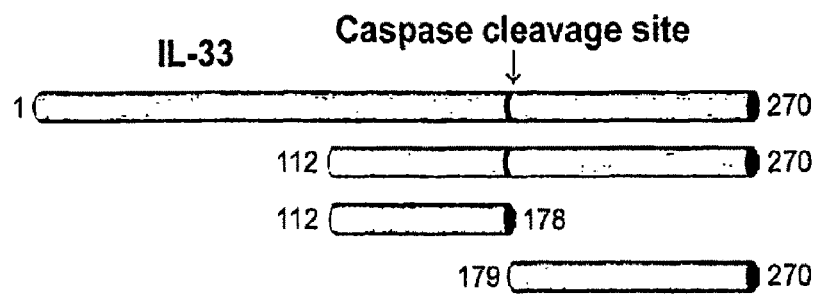
Figure 23:
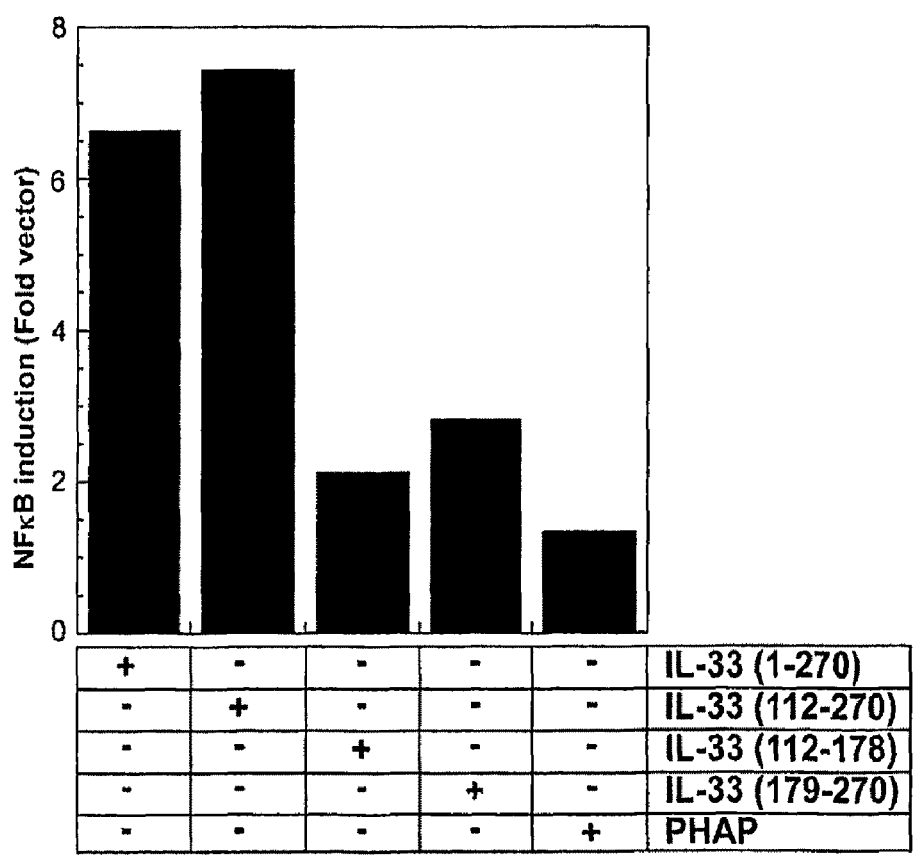
Figure 24:
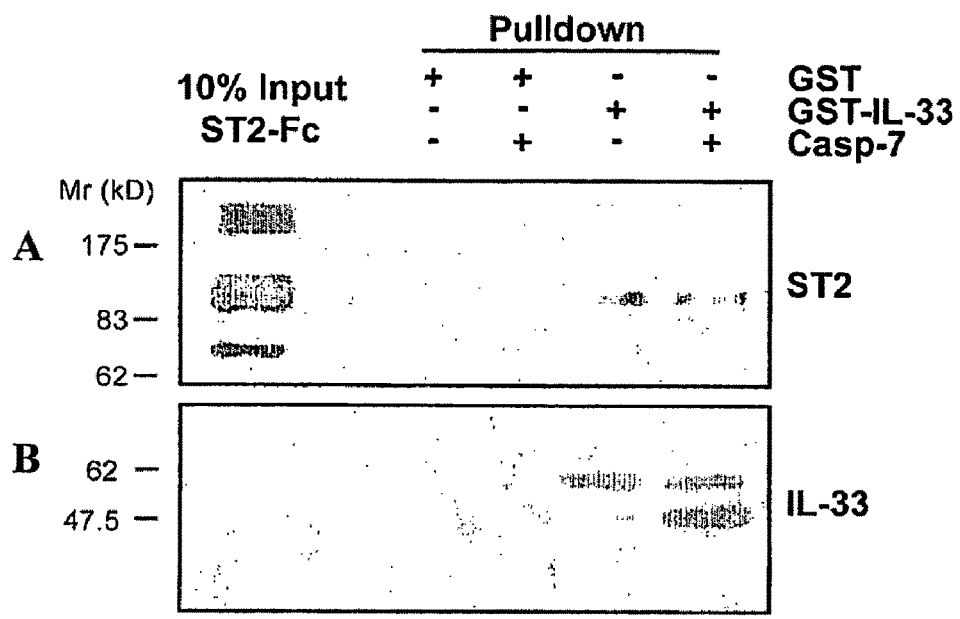
Figure 25:
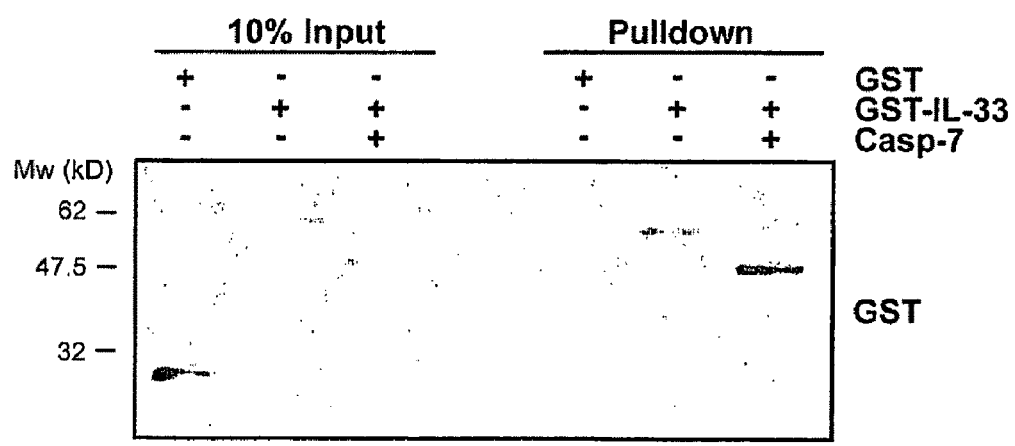

FIG. 2 is a graph showing hydrolysis of the synthetic caspase substrate, WEHD-AMC, by recombinant caspase-1, -4 and -5 (20 nM each). Note that recombinant inflammatory caspases cleave WEHD-AMC with different efficiencies. Active site titrations with zVAD-fmk confirmed that the molar amounts of each caspase were identical;

FIG. 3 is an immunoblot of recombinant caspases-1, -3 and -7 that were added to THP-1 cell-free extracts, at the indicated concentrations, followed by incubation at 37° C. for 2 h. Extracts were then analysed by SDS-PAGE followed by immunoblotting for the indicated substrate proteins;

FIG. 4 is a fluorograph of an SDS-PAGE gel of $^{35}$S-labeled hIL-33 (SEQ ID NOS 1 and 2), mIL-33 (SEQ ID NOS 5 and 6) and IL-1β, prepared by in vitro transcription/translation, and incubated with the indicated concentrations of recombinant caspase-1, -3 and -7 for 2 h at 37° C. followed by analysis;

FIG. 5 are bar charts illustrating Densitometric analysis of the SDS-PAGE gels of FIG. 4. Scanned gels were analysed using ImageJ software (http://rsb.info.nih.gov/ij/) and results were expressed as % proteolysis of the full-length forms of each protein relative to the untreated control. (A) caspase 1; (B) caspase 3; (C) caspase 7;

FIG. 6 is an immunoblot of cell-free extracts derived from THP-1 cells that were incubated at 37° C. to permit spontaneous activation of inflammatory caspases ('Inflammasome') or in the presence of 50 μg/ml cytochrome c and 1 mM dATP to promote activation of apoptotic caspases ('Apoptosome'). As a control, caspase activation was suppressed through addition of 5 μM YVAD-CHO. Extracts were then immunoblotted for caspase-1, caspase-3 and IL-1β, as indicated;

FIG. 7 is a fluorograph of an SDS-PAGE gel of $^{35}$S-labeled hIL-33 (SEQ ID NOS 1 and 2), mIL-33 (SEQ ID NOS 5 and 6) and IL-1β which were added to THP-1 cell-free extracts followed by treatment as described for FIG. 6. Reactions were sampled at the indicated times and were subsequently analysed by SDS-PAGE/fluorography;

FIG. 8 is an immunoblot of cell-free extracts that were derived from Jurkat cells were incubated at 37° C. in the presence (Apoptosome) or absence (Control) of cytochrome c/dATP, as indicated, followed by immunoblotting for caspase-3, caspase-9, XIAP or p23;

FIG. 9 is a fluorograph of an SDS-PAGE gel of $^{35}$S-labeled hIL-33 (SEQ ID NOS 1 and 2) or mIL-33 (SEQ ID NOS 5 and 6) that were added to Jurkat cell-free extracts which were treated as described for FIG. 8. Reactions were sampled at the indicated times and were subsequently analysed by SDS-PAGE followed by fluorography;

FIG. 10 is a schematic representation of human (hIL-33) and murine (mIL-33) IL-33 depicting potential caspase cleavage motifs. The proposed site of caspase-1-mediated proteolysis (ALHD[110]; Schmitz et al., 2005) is not conserved between human and mouse IL-33;

FIG. 11 is a fluorograph of an SDS-PAGE gel of $^{35}$S-labeled full length (FL) hIL-33 (SEQ IN NOS 1 and 2) and the indicated IL-33 deletion mutants (SEQ ID NOS 12 and 13) which were incubated in the presence of recombinant caspase-7 (40 nM) for 2 h at 37° C. followed by analysis by SDS-PAGE/fluorography;

FIG. 12 is a Coomassie blue stained gel of recombinant GST-IL-33 that was incubated for 2 h at 37° C. in the presence or absence of recombinant caspase-7 (600 nM), as indicated, followed by SDS-PAGE/Coomassie blue staining;

FIG. 13 are graphs of recombinant GST-IL-33 being cleaved by caspase-7, as depicted in FIG. 12, followed by analysis of the cleavage products by MALDI-TOF mass spectrometry. Mass spectrograms for each IL-33 species (i.e. full length, large and small fragments (all SEQ ID NO. 6)) are shown, along with the corresponding peptide coverage of each. The peptide coverage (highlighted in bold) of each species indicates that the site of caspase-7-mediated proteolysis lies between residues 159 and 187;

FIG. 14 is a fluorograph of an SDS-PAGE gel of $^{35}$S-labeled wild-type hIL-33 (SEQ ID NOS 1 and 2) and IL-33$^{D178A}$ point mutant (SEQ ID NOS 3 and 4) that were incubated for 2 h at 37° C. with recombinant caspase-3, -7 and -1, as shown. Reactions were analysed by SDS-PAGE/fluorography;

FIG. 15 is a fluorograph of an SDS-PAGE gel of $^{35}$S-labeled wild-type hIL-33 (SEQ ID NOS 1 and 2) and IL-33$^{D178A}$ point mutant (SEQ ID NOS 3 and 4) that were added to Jurkat cell-free extracts followed by activation of apoptotic caspases by addition of cytochrome c and dATP. Reactions were sampled at the indicated times and were subsequently analysed by SDS-PAGE/fluorography. Samples of the same reactions were also immunoblotted for caspase-3 and XIAP, as indicated;

FIG. 16 is a Coomassie blue stained gel of recombinant IL-33$^{112-270}$ (SEQ ID NO. 14) and IL-33$^{112-270}$ D178A point mutant that were incubated with recombinant caspase-7 (600 nM) for 4 h at 37° C. followed by analysis by SDS-PAGE/Coomassie blue staining;

FIGS. 17 A and B are bar charts of HeLa cells that were transfected with expression plasmids encoding either wild type IL-33 (SEQ ID NOS 1 and 2) (A), or IL-33$^{D178A}$ point mutant (SEQ ID NOS 3 and 4) (B). 24 h later, cells were then treated with Daunorubicin (Dauno; 5 μM), TNF (10 ng/ml), cycloheximide (CHX; 1 μM) and cisplatin (50 μM) and incubated for a further 8 h before assessment of apoptosis;

FIGS. 18 A and B are Western blots of cell lysates derived from HeLa cells transfected either with wild type IL-33 (SEQ ID NOS 1 and 2) (A) or the D178A point mutant (SEQ ID NOS 3 and 4) (B), followed by incubation in the presence or absence of Daunorubicin (Dauno), TNF/cycloheximide, or Cisplatin at concentrations indicated in FIG. 17;

FIG. 19 is a bar chart of HeLa cells that were transfected with an IL-33 expression plasmid for 24 h followed by treatment for 8 h with Daunorubicin (5 μM) to induce apoptosis. In parallel, HeLa cells were also treated with the poly-caspase inhibitor Z-VAD-fmk (50 μM), or were transfected with a Bcl-xL expression plasmid as indicated;

FIG. 20 is an immunoblot of cell lysates that were generated from the cells of FIG. 19 and were immunoblotted for the indicated proteins;

FIG. 21 is a bar chart of HEK293T cells that were transfected with a ST2L receptor expression plasmid (200 ng per well) along with an NFκB luciferase reporter plasmid (10 ng) in a 6 well plates. 24 h after transfection, the indicated concentrations of recombinant GST-IL-33 and caspase-7-cleaved GST-IL-33 were added for a further 8 h. Luciferase activity was assayed in cell lysates and normalised against empty vector transfected cells;

FIG. 22 is a schematic representation of IL-33 depicting the caspase cleavage site and the various His-tagged IL-33 deletion mutants generated for this study;

FIG. 23 is a bar chart of cells that were transfected as in FIG. 21, followed by addition of 100 ng/ml of the indicated IL-33 recombinant proteins or the control protein, PHAP. Cell lysates were assayed for luciferase activity 8 h after addition of recombinant proteins;

FIGS. 24 A and B are immunoblots of (A) capture of soluble ST2-Fc after incubation with sepharose-immobilized GST, GST treated with caspase-7, GST-IL-33, or GST-IL-33 treated with caspase-7, followed by probing for ST2; and (B) cleavage status of the IL-33 used for the pulldown assay was revealed by blotting for this protein. Note that ST2-Fc was pulled down with both the full length as well as the cleaved form of IL-33 (A);

FIG. 25 is an immunoblot of protein A/G immobilized ST2-Fc that was used to assess binding of GST, GST-IL-33 full-length or cleaved GST-IL-33. Note that both full length as well as the cleaved forms of IL-33 were captured by ST2 whereas the GST control was not.

Figure 26:
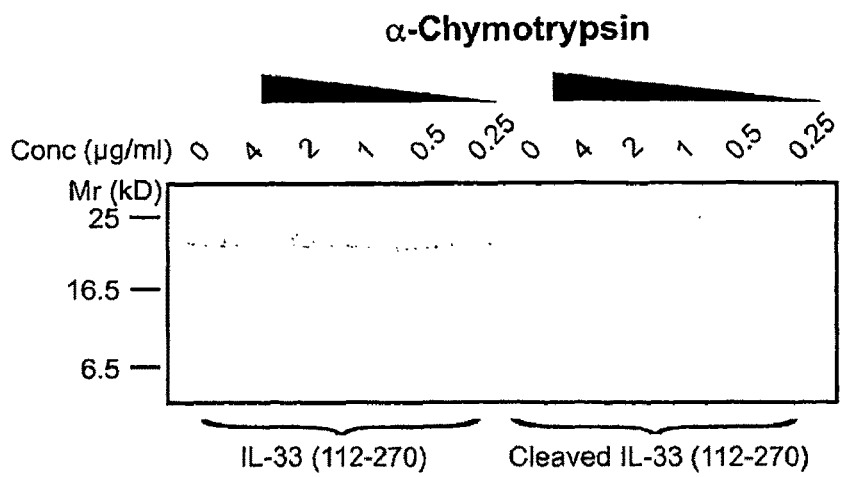
Figure 27:
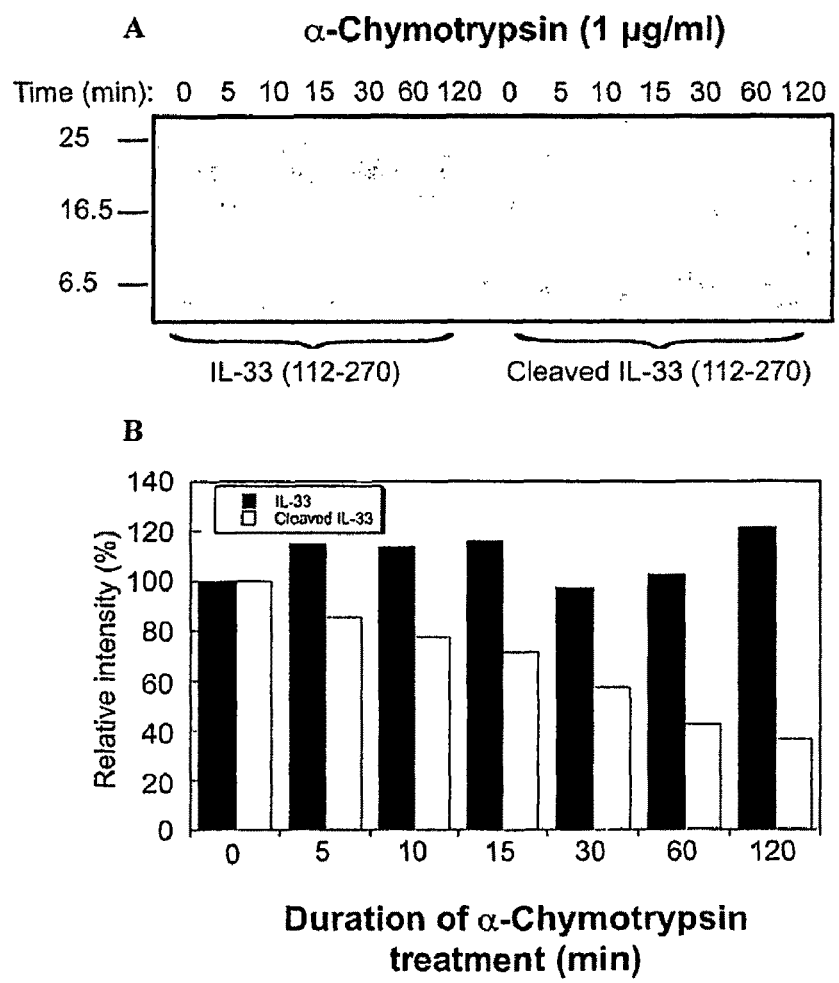
Figure 28:
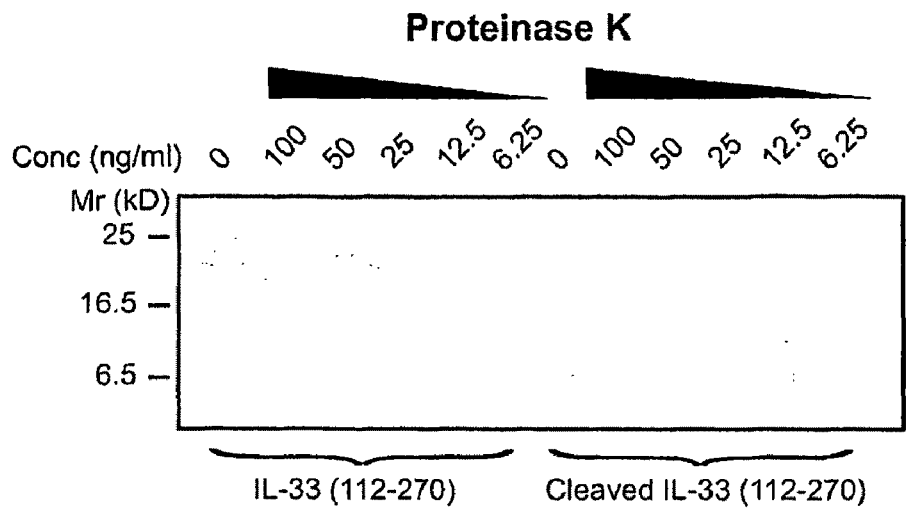
Figure 29:
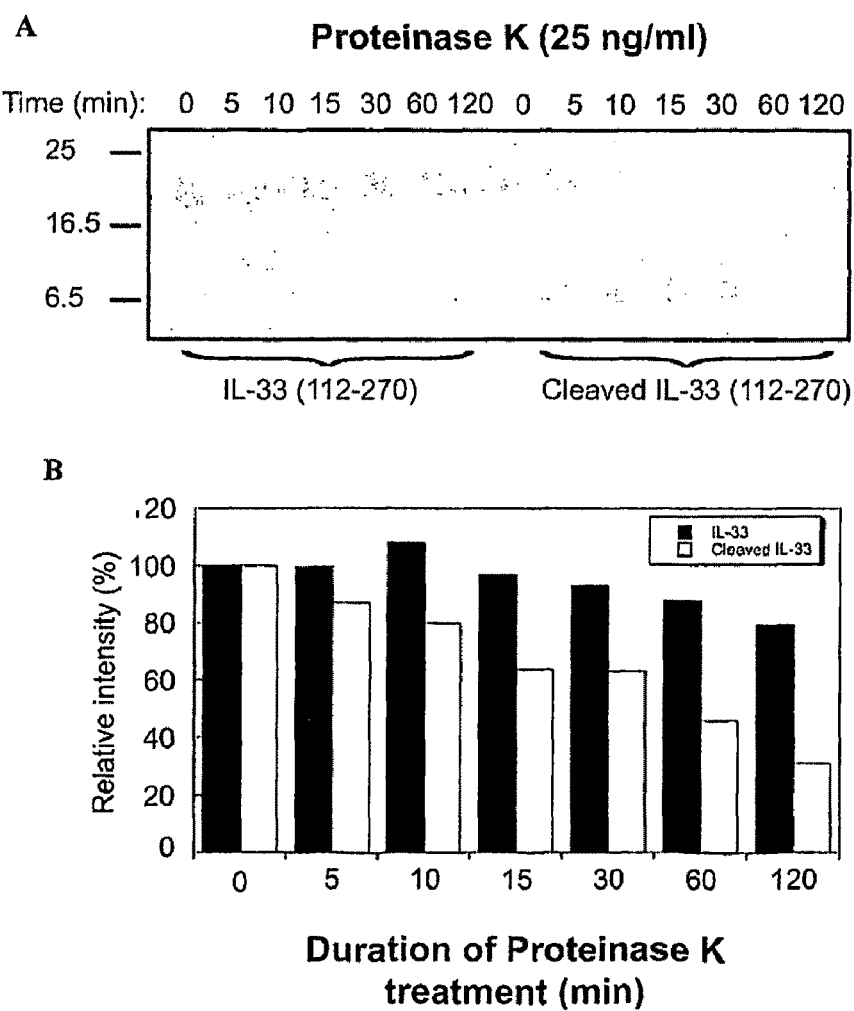
Figure 30:
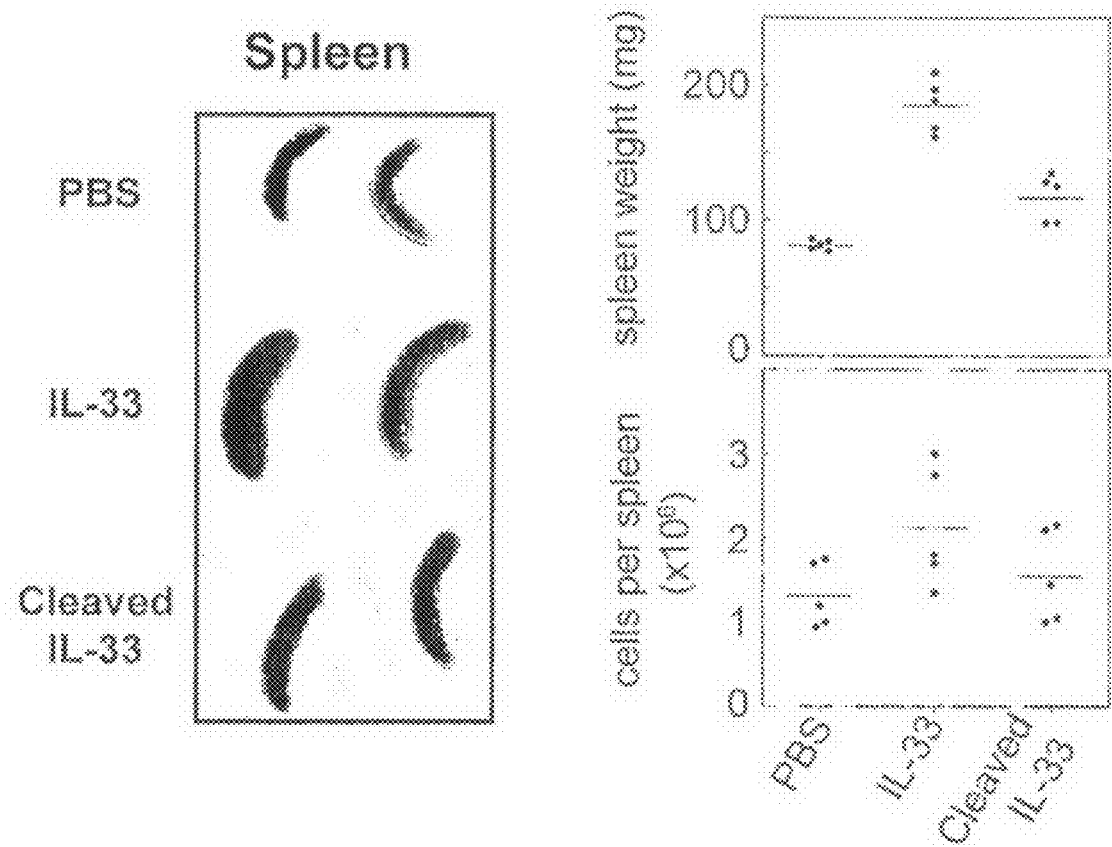
Figure 31:
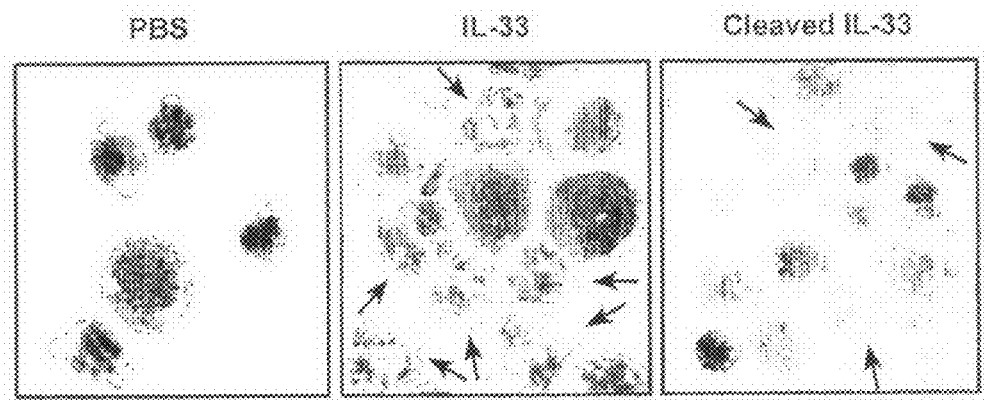
Figure 31:
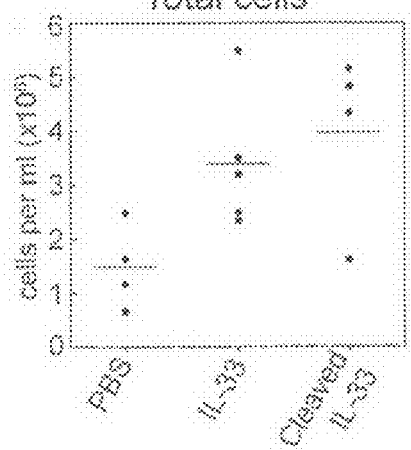
Figure 31:
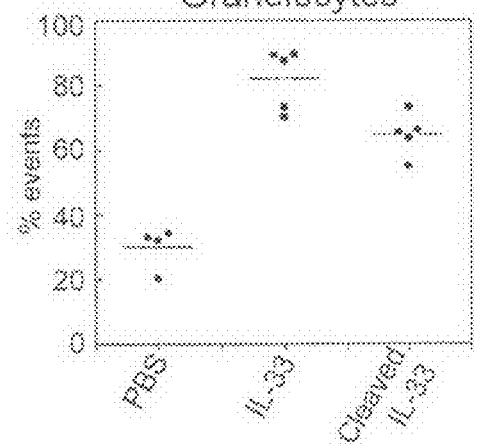
Figure 32:
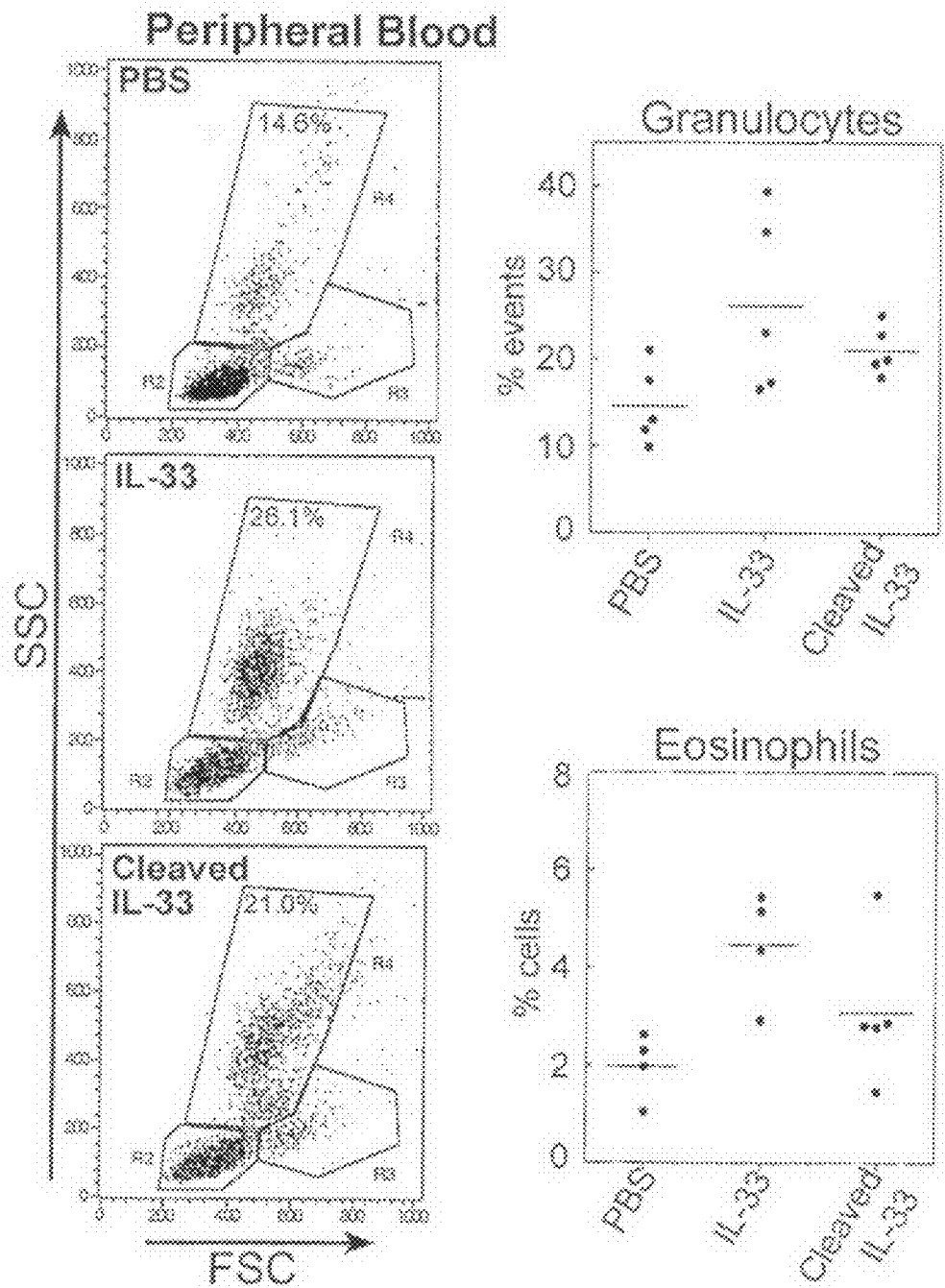
Figure 33:
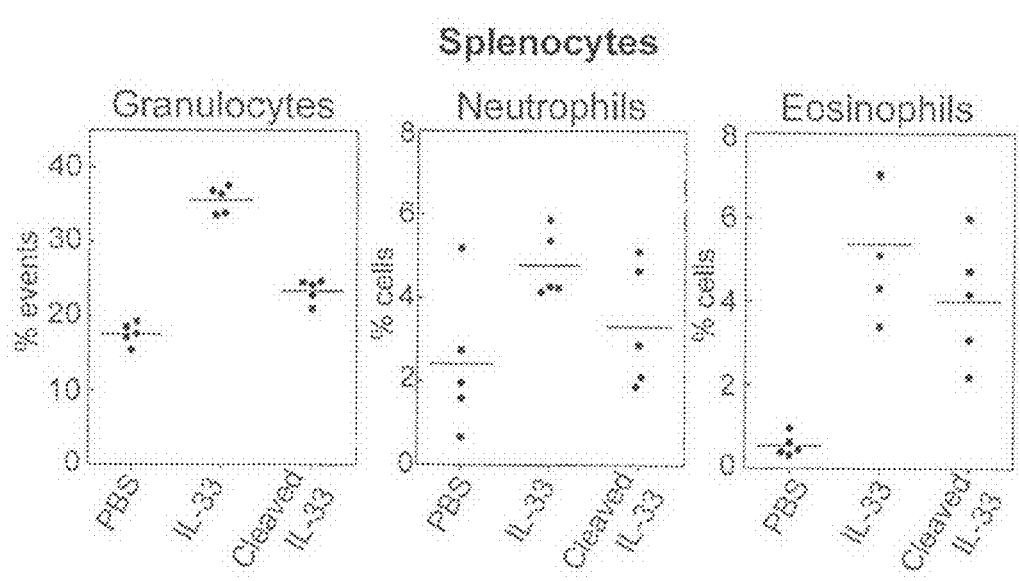
Figure 34:
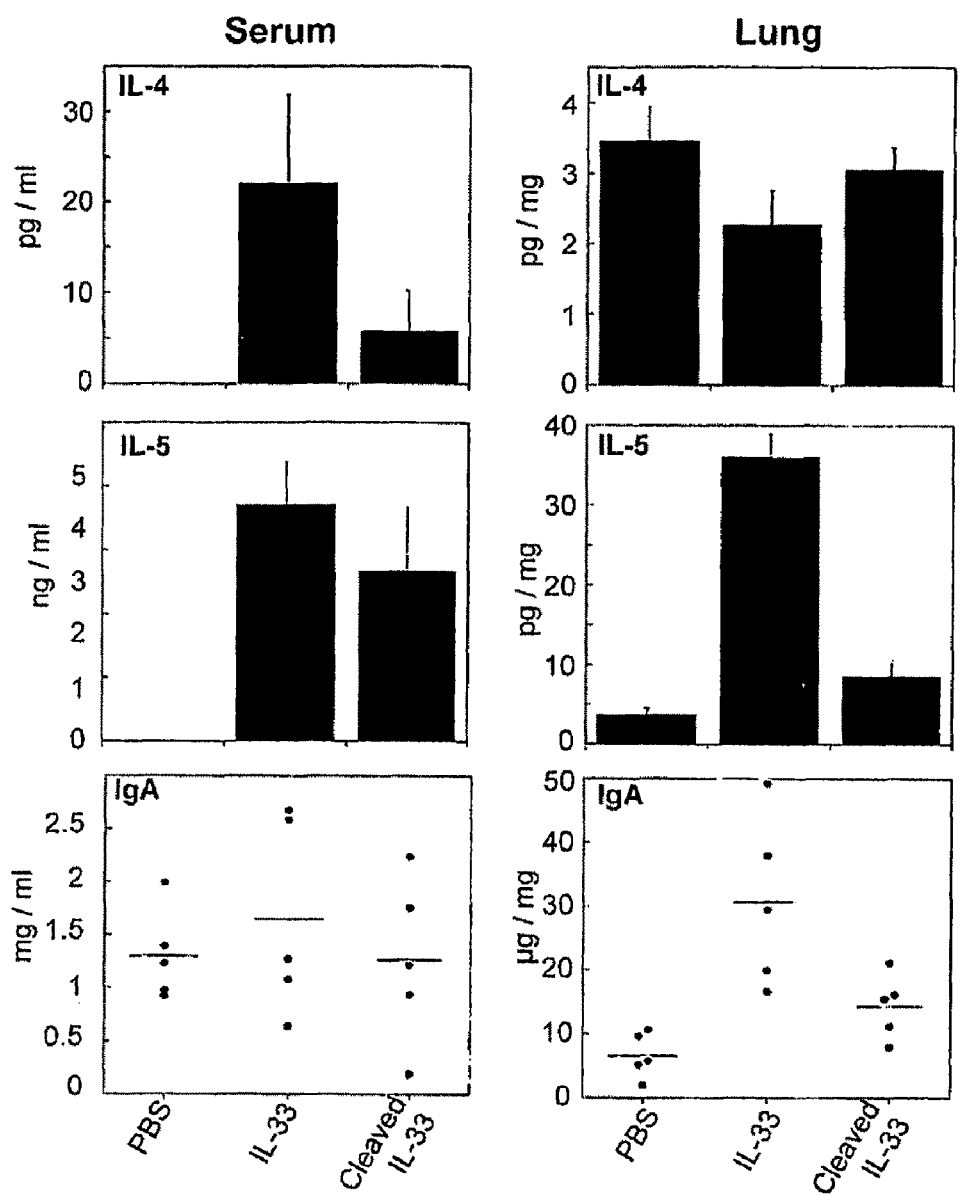
Figure 35:
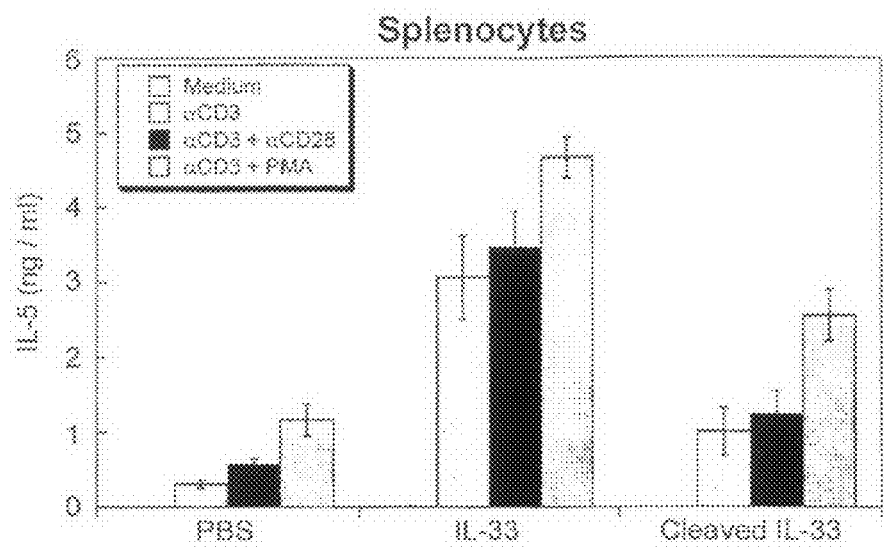
Figure 35:
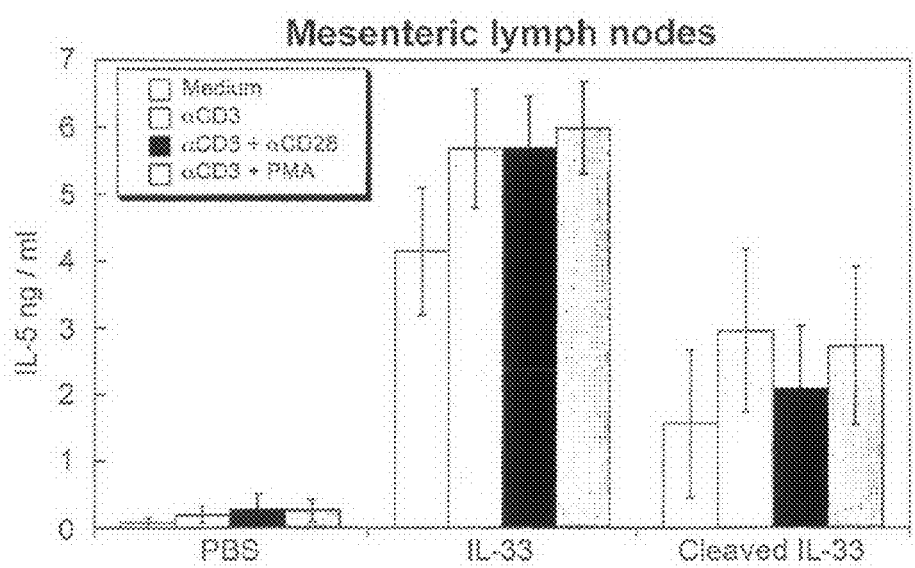

FIG. 26 is a Coomassie blue stained gel of purified recombinant IL-33$^{112-270}$, or caspase-cleaved IL-33$^{112-270}$, that were incubated for 2 h at 37° C. in the presence of the indicated concentrations of α-chymotrypsin, followed by analysis by SDS-PAGE/Coomassie blue staining;

FIG. 27 (A) is a Coomassie blue stained gel of purified recombinant IL-33$^{112-270}$, or caspase-cleaved IL-33$^{112-270}$, that were incubated for the indicated times at 37° C. with α-chymotrypsin (1 μg/ml) followed by analysis by SDS-PAGE/Coomassie blue staining, (B) is a histogram representing the relative intensities of each IL-33 species normalized to the 0 h time point. Gels were quantitated using Image-J software;

FIG. 28 is a Coomassie blue stained gel of purified recombinant IL-33$^{112-270}$ and caspase-cleaved IL-33$^{112-270}$ that were incubated for 2 h at 37° C. in the presence of the indicated concentrations of proteinase K followed by analysis of cleavage reactions by SDS-PAGE/Coomassie blue staining;

FIG. 29 (A) is a Coomassie blue stained gel of purified recombinant IL-33$^{112-270}$, or caspase-cleaved IL-33$^{112-270}$, that were incubated at 37° C. with proteinase K (25 ng/ml) for the indicated times followed by analysis by SDS-PAGE/Coomassie blue staining; (B) is a histogram representing the relative intensities of each IL-33 species normalized to the 0 h time point. Gels were quantitated using Image-J software;

FIG. 30 are photographs of spleen size and bar charts of weight and cellularity for C57BL/6 mice (5 per treatment group) were injected (i.p.) either with PBS, IL-33$^{112-270}$ (1 μg per mouse per day), or caspase-cleaved IL-33$^{112-270}$ (1 μg per mouse per day) or for 6 consecutive days. Note that the artificially-truncated IL-33 was used here due to problems associated with purification of large quantities of full length IL-33. Each data point within the bar chart represents an individual mouse within each group of mice. Photographs show representative spleens for two mice per group;

FIG. 31 (A) are photographs of peritoneal lavage-derived cells from the mice of FIG. 30 that were enumerated by haemocytometer and cytospins were also made. Cytospins were stained with hematoxylin and eosin for assessment of cell morphology, arrows indicate granulocytes (A). Granulocyte numbers were also determined by forward scatter and side scatter (FSC/SSC) analysis (B, right panel) the left panel of (B) represents data from manual counts determined by enumeration with a haemocytometer;

FIG. 32 are plots of peripheral bloods from the mice of FIG. 30 that were treated with FACS lysis solution to eliminate RBCs followed by analysis by flow cytometry. Granulocyte numbers were scored based on their high FSC/SSC properties, as shown. Eosinophil numbers were determined by counting H&E-stained cytospin preparations of peripheral bloods;

FIG. 33 are graphs of spleen-derived granulocytes were enumerated as described for FIG. 32 and neutrophil and eosinophil numbers were scored on H&E-stained cytospin preparations;

FIG. 34 are graphs illustrating IL-4, IL-5 and IgA levels that were determined by ELISA in plasma samples or lung homogenates for the mice of FIG. 30. Note that lung data are expressed per mg protein; and FIGS. 35 A and B are graphs showing splenocyte (A) and mesenteric lymph node cells (B) ($10^6$ cells/ml) from the mice of FIG. 30 that were restimulated either with medium, 1 μg/ml anti-CD3, 1 μg/ml anti-CD3 and 1 μg/ml anti-CD28, or 1 μg/ml anti-CD3 and 20 ng/ml PMA, as indicated. Supernatants were collected after 3 days and IL-5 concentrations were determined by ELISA.

LISTING OF SEQUENCE IDENTIFIERS

SEQ ID NO.1 is human IL-33 nucleic acid (cDNA) sequence;
SEQ ID NO. 2 is human IL-33 amino acid sequence;
SEQ ID NO. 3 is a modified human IL-33 nucleic acid (cDNA) sequence (alteration of base 533 from a to c);
SEQ ID NO. 4 is a modified human IL-33 amino acid sequence (alteration of residue 178 from Asp to Ala);
SEQ ID NO.5 is mouse IL-33 nucleic acid (cDNA) sequence;
SEQ ID NO. 6 is mouse IL-33 amino acid sequence;
SEQ ID NO. 7 is a modified human IL-33 nucleic acid (cDNA) sequence (alteration of base 524 from a to c);
SEQ ID NO. 8 is a modified mouse IL-33 amino acid sequence (alteration of residue 175 from Asp to Ala);
SEQ ID NO. 9 is human IL-33 residues 58 to 72 amino acid sequence;
SEQ ID NO. 10 is human IL-33 residues 175 to 178 amino acid sequence;
SEQ ID NO. 11 is mouse IL-33 residues 172 to 175 amino acid sequence;
SEQ ID NO. 12 is human IL-33 residues 1 to 178 amino acid sequence;
SEQ ID NO. 13 is human IL-33 residues 179 to 270 amino acid sequence;
SEQ ID NO. 14 is human IL-33 residues 112 to 270 amino acid sequence;
SEQ ID No. 15 is human IL-33 residues 112 to 178 amino acid sequence;
SEQ ID NO. 16 is human IL-33 residues 155 to 198 amino acid sequence; and
SEQ ID NO. 17 is human IL-33 residues 165 to 188 amino acid sequence.

DETAILED DESCRIPTION

We have examined the role of caspase-1 and of the other inflammatory caspases (caspase-4 and caspase-5) in the maturation of IL-33. Surprisingly, we find little evidence that IL-33 is a physiological substrate for the inflammatory caspases. Rather, here we show that this cytokine is efficiently processed by caspases that are selectively activated during apoptosis. Furthermore, caspase-mediated proteolysis of IL-33 increased its sensitivity to degradation by serum proteases and dramatically attenuated IL-33 biological activity in vivo. Thus, IL-33 is preferentially processed by caspases activated during apoptosis rather than inflammation and this may serve to reduce, rather than enhance, IL-33 activity in vivo.

Here we have shown that IL-33 is a poor substrate for the inflammatory caspases but is efficiently cleaved by the cell death-associated caspases (caspases-3 and -7). We have mapped the site of caspase-mediated proteolysis within IL-33 to a motif (DGVD$^{178}$ in human and DGVD$^{175}$ in mouse) that is fully conserved between the human and mouse forms of this protein. Furthermore, contrary to previous suggestions, proteolysis of IL-33 was not required for ST2 receptor binding or ST2 receptor-dependent NFκB activation. Proteolysis of IL-33 by caspases did not abolish the binding of this protein to ST2 but did reduce its ability to initiate ST2-dependent NFκB activation and also substantially reduced the half-life of this cytokine in the presence of the serum proteases α-chymotrypsin and proteinase K. This suggests that caspases are involved in regulating the half-life of IL-33, through increasing the susceptibility of this cytokine to degradation by other proteases.

Because caspases are activated during apoptosis but not necrosis, an interesting implication of our experiments is that the half-life of IL-33 is reduced when cells capable of producing this cytokine undergo apoptosis. Consistent with this view, IL-33 failed to undergo proteolytic processing in necrotic cells but was readily cleaved during apoptosis. Similar to IL-1α and IL-1β, IL-33 does not possess a classical secretory sequence and is therefore unlikely to be released from cells via the classical ER-Golgi secretory pathway. Therefore, one possibility is that IL-33, similar to the non-classical cytokine HMGB1 (Scaffidi et al., 2002), is released through necrosis of cells expressing this protein. Because caspases do not become activated during necrotic cell death (Kroemer and Martin, 2005), IL-33 is therefore likely to be released from necrotic cells as a full-length molecule. However, because IL-33 is efficiently processed by apoptotic caspases, particularly caspase-7, such cells are likely to release the caspase-cleaved form of this cytokine that exhibits reduced potency. Thus, proteolysis of IL-33 during apoptosis may represent a means of reducing the pro-inflammatory activity of this cytokine, through changing the conformation of the protein and accelerating its degradation by serum proteases. Interestingly, it has been demonstrated by several groups that apoptotic cells are much less pro-inflammatory than necrotic cells and can even exhibit anti-inflammatory effects that may dominate over necrotic cell-derived factors (Voll et al., 1997; Patel et al., 2007). Thus, the proteolysis of IL-33 during apoptosis may contribute to the damping down of the potentially pro-inflammatory effects of cell death. It is also possible that proteolysis of IL-33 by caspases renders this molecule susceptible to degradation by other intracellular (i.e non-caspase) proteases. Furthermore, because apoptotic cells are typically engulfed by phagocytes prior to loss of plasma membrane integrity (Taylor et al., 2008), this further reduces the possibility of biologically active IL-33 being released from such cells. IL-33 may therefore represent an endogenous 'danger signal' or 'alarmin' that is more potent when released in the context of pathological cell death (necrosis) as opposed to apoptosis which is more usually encountered in physiological settings (Taylor et al., 2008).

Interestingly, IL-33 is a nuclear protein and has been reported to possess activity as a regulator of transcription within cells expressing this molecule (Carriere et al., 2007). IL-1α also exhibits a nuclear expression pattern and is reported to have intracellular activities (Maier et al., 1994). Furthermore, although the precursor-form of IL-1β is inactive, pro-IL-1α is active as a full-length protein and is capable of binding to the IL-1 receptor (Mosley et al., 1987a,b). It is also suspected that the major route of IL-1α release may be through necrosis. Thus, IL-33 and IL-1α share several features in common as both proteins are active as full-length molecules but also undergo proteolytic processing under certain circumstances.

In conclusion, here we have shown that IL-33 is active as a full-length cytokine, similar to IL-1α, and does not require proteolytic maturation by inflammatory caspases for production of the biologically active cytokine. Furthermore, IL-33 is efficiently cleaved at a conserved motif by apoptotic but not inflammatory caspases, thereby rendering this cytokine susceptible to protease-mediated degradation and attenuation of biological activity. Consistent with this, IL-33 was processed at this cleavage motif within apoptotic but not necrotic cells. Thus, contrary to the previous proposal that caspases activate IL-33 (Schmitz et al., 2005), caspase-mediated proteolysis acts to dampen the pro-inflammatory properties of this cytokine.

The invention will be more clearly understood from the following examples.

EXPERIMENTAL PROCEDURES

Reagents

Antibodies specific to caspase-3, caspase-7 and XIAP were purchased from BD (UK). Anti-caspase-1 antibodies were purchased from Santa Cruz (UK). Antibodies specific to caspase-4 and caspase-5 were purchased from MBL (UK). Anti-IL-1β antibodies were purchased from R&D systems (UK), anti-caspase-9 monoclonal antibodies were purchased from Oncogene Research Products (UK). Anti-co-chaperone p23 antibodies were purchased from Affinity Bioreagents (UK). Anti-actin antibody was purchased from ICN (UK). Anti-GR-1-FITC antibody was purchased from Immuno-Tools (Germany). The peptides, z-YVAD-CHO, Ac-WEHD-AMC, Ac-DEVD-AFC zVAD-FMK were all purchased from Bachem (UK). Unless otherwise indicated, all other reagents were purchased from Sigma (Ireland) Ltd.

Generation of Antibodies to IL-33

Polyclonal antibodies were generated against hIL-33 by repeated immunization of rabbits with the hIL-33 peptide $^{58}$CYFRRETTKRPSLKT$^{72}$ (SEQ ID NO. 9) (Sigma Genosys, UK).

Expression and Purification of Recombinant IL-33

GST-IL-33 was generated by inserting the human IL-33 coding sequence (SEQ ID NO. 1) into the pGEX4T2 bacterial expression vector. GST-IL-33 was expressed by addition of 100 μM IPTG to exponentially growing cultures of DH5α strain E. coli followed by incubation for 1 h at room temperature. Bacteria were lysed by sonication and GST-IL-33 was captured using Glutathione Sepharose 4B, followed by elution into PBS, pH 7.2, in the presence of 20 mM reduced gluthathione. Protein was then extensively dialysed against PBS prior to use. His-tagged IL-33 deletion mutants were generated through inserting the relevant coding sequences into pET45b (Novagen, UK), followed by expression in BL21pLysS strain E. coli and were purified using Ni$^{2+}$ beads (Qiagen, UK) according to standard procedures. Proteins were then eluted from the affinity capture matrix and were extensively dialysed against PBS, pH 7.2, followed by depletion of LPS by several rounds of incubation to agarose-immobilized polymyxin B (Sigma). For caspase-mediated processing, recombinant IL-33 was incubated with recombinant caspase-7 (600 nM) for 4 h at 37° C., or with an identical concentration of heat-inactivated caspase-7 as a control.

Cell-Free Reactions

Cell-free extracts were generated from exponentially growing healthy THP-1 cells as described previously (Murphy et al., 2003; Slee et al., 1999). Briefly, THP-1 cells were treated for 5 hours with 1 μg/ml LPS then harvested by centrifugation at 800×g into a Dounce-type homogenizer. Three volumes of ice-cold cell extract buffer were added CEB (20 mM Hepes, pH 7.5, 10 mM KCl, 1.5 mM MgCl$_2$, 1 mM EDTA, 1 mM EGTA, 1 mM DTT, 100 µM PMSF, 10 µg/ml leupeptin, 2 µg/ml aprotinin), and the cells were allowed to swell for 15-20 min on ice. Cells were then lysed by homogenization with 10-15 strokes of a B-type pestle. Lysates were clarified by centrifugation at 15,000×g for 30 min to remove nuclei, mitochondria, and other cellular debris. Extracts were then aliquoted and frozen at −70° C. prior to use. For in vitro activation of caspases involved in inflammation, THP-1 cell-free extracts were diluted to 80% in CEB and incubated at 37° C. for 2 hours. To provoke apoptosome-dependent caspase activation, bovine heart cytochrome c and dATP were added to reactions to final concentrations of 50 µg/ml and 1 mM, respectively.

Expression and Purification of Recombinant Caspases

Caspase-1.p30, Caspase-4.p30, Caspase-5.p30, Caspase-3 and Caspase-7 were produced by PCR-mediated amplification of the relevant coding sequences from the respective full-length cDNA, followed by subcloning of the resulting PCR products in-frame with the His coding region of pET15b (Novagen, UK) for Caspase-1, pet23b (Novagen, UK) for Caspase-3 and -7, or pGEX4T1 (Amersham, UK) for Caspase-4 and -5. Plasmids encoding His-tagged and were transformed into *Escherichia coli* DH5α. GST-tagged fusion proteins were transformed into BL21pLysS and bacteria were induced to express the recombinant proteins in the presence of 0.1 to 0.6 mM IPTG (Melford, UK). Recombinant caspases were subsequently purified using Ni$^{2+}$ beads (Qiagen, UK) or Glutathione Sepharose 4B (Amersham, UK) according to standard procedures.

Caspase Activity Assays

For the assessment of caspase activity, recombinant caspases-1, -3, -4 and -5 and -7 were diluted to a final volume of 50 µl in CEB containing 50 µM Ac-WEHD-AMC (for the inflammatory caspases) or Ac-DEVD-AFC (for apoptotic caspases). Samples were then measured over 30 minutes in an automated fluorimeter (Spectrafluor Plus, TECAN, UK) at wavelengths of 360 nm (excitation) and 465 nm (emission). Caspases were active site titrated by incubation with a range of concentrations (0, 6.25, 12.5, 25, 50, 100 nM) of the poly-caspase inhibitor zVAD-fmk for 30 min at 37° C., followed by measurement of residual caspase activity by monitoring the hydrolysis of WEHD-AMC or Ac-DEVD-AFC as described above.

Coupled In Vitro Transcription/Translation Reactions

In vitro transcription/translation reactions were carried out using purified plasmid templates added to a rabbit reticulocyte lysate system (Promega, UK) with $^{35}$S-Methionine (Amersham, UK) as described previously (Slee et al., 1999).

Pull Down Assays

GST-IL-33 (1 µg) was immobilised on 30 µl Glutathione Sepharose 4B (Amersham Biosciences, UK) by rotation at 4° C. for 30 minutes, followed by addition of 1 µg of recombinant ST2.Fc (Alexis, UK) and further incubation for 4 h in 1 ml of reaction buffer (50 mM Tris, pH 7.6, 120 mM NaCl, 0.1% CHAPS). The reciprocal pull down experiments were done under essentially the same conditions.

Transient Transfection and Reporter Gene Assays

HeLa cells were seeded at a density of 2×10$^5$ cells per well of a 6-well tissue culture plate and were transiently transfected 24 h later with GeneJuice (Merck, Ireland), according to the manufacturer's instructions. HEK293T cells were seeded at a density of 4×10$^5$ cells per well of a 6-well tissue culture plate 24 h prior to transfection. Cells were transfected with plasmids according to the standard calcium phosphate precipitation method, and DNA complexes were allowed to remain on cells for 14 h before replacing with fresh medium. For the luciferase reporter assay the cells were lysed in 200 µl RLS (100 mM HEPES, pH 8, 2 mM MgCl$_2$, 2% Triton X-100) of which 20 µl were assayed with 50 µl LAR (20 mM N-Glycylglycine, 1 mM MgCl$_2$, 100 µM EDTA, 27.8 µg/ml ATP, 21.3 µg/ml Coenzyme A and 160 µg/ml beetle luciferin (Promega, UK). Luminescence was measured in a Spectrafluor Plus (TECAN, UK).

Animals and In Vivo Treatment

C57BL/6 mice were obtained from Harlan U.K. Animal experiments and maintenance were approved and regulated by the Trinity College Dublin ethics committee and the Irish Department of Health.

Analysis of Peripheral Blood, Spleen and Peritoneal Lavage Samples

Blood was collected from the tail vein followed by addition of 100 µM EDTA as an anticoagulant. Red blood cells were lysed in 20 volumes of 150 mM NH$_4$CL, 10 mM NaHCO$_3$ and 100 µM EDTA. Cytospins were prepared and stained with hematoxylin/eosin and scored for lymphocytes, monocytes, neutrophils and eosinophils. For flow cytometry, cells were fixed in FACS lysis buffer (BD, UK) according to the manufacturer's instructions and analysed on a FACScalibur (BD, UK).

Determination of Cytokine and IgA Levels

Cytokines were detected by enzyme-linked immunoabsorbent assay (ELISA) with paired antibodies for IL-4 and IL-5 (BD Pharmingen, UK), IgA levels were measured as described previously (Lavelle et al., 2001).

Example 1

IL-33 is a Poor Substrate for Caspase-1

It has been proposed that IL-33, similar to IL-1α, requires proteolytic-processing by caspase-1 to produce the mature form of this cytokine (Schmitz et al., 2005). However, this idea is based solely upon the observation that IL-33 can be cleaved by high concentrations of caspase-1 in vitro (Schmitz et al., 2005). It is not clear whether IL-33 is processed at physiological concentrations of caspase-1 or whether this cytokine requires proteolytic processing for activation, nor is it known whether IL-33 is a substrate for any of the other members of the caspase family of proteases.

Figure 1:
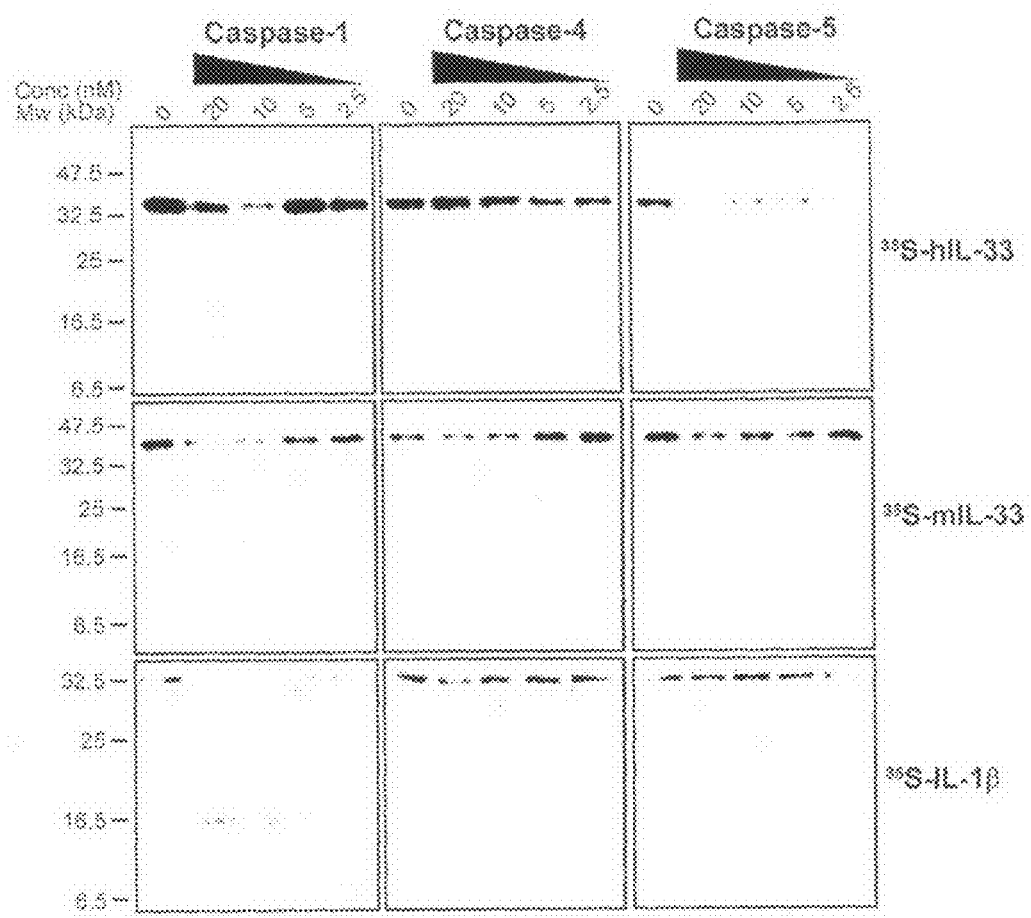
FIG. 1 is a fluorograph of an SDS-PAGE gel of $^{35}$S-labeled hIL-33 (SEQ ID NOS 1 and 2), mIL-33 (SEQ ID NOS 5 and 6) and IL-1β which were prepared by in vitro transcription/ translation and incubated with the indicated concentrations of recombinant caspase-1, -4 and -5 for 2 h at 37° C. followed by analysis.

To explore these issues, we incubated in vitro transcribed and translated human (SEQ ID NO. 2) and mouse IL-33 (SEQ ID NO. 6) in the presence of a range of concentrations of the inflammatory caspases-1, -4 and -5 (FIG. 1). For these experiments, non-saturating concentrations of caspase-1 were chosen that achieved robust proteolysis of the known caspase-1 substrate, IL-1β. We also incubated IL-33 with equimolar amounts of the other inflammatory caspases (caspases-4 and -5). All caspases were active within the concentration ranges used, as indicated by hydrolysis of the synthetic peptide substrate WEHD-AMC (FIG. 2). However, while caspase-1 readily cleaved IL-1β, human (SEQ ID NO. 2) and murine (SEQ ID NO. 6) IL-33 failed to undergo significant proteolytic processing under the same conditions (FIG. 1). Caspases-4 and -5 also failed to process IL-33 suggesting that, in comparison with IL-1β, IL-33 is a poor substrate for the inflammatory caspases.

Example 2

IL-33 is a Substrate for Caspases Activated During Apoptosis

We next explored whether IL-33 could be cleaved by caspases that participate in apoptosis rather than inflammation. Caspase-3 and -7 act as the major effector caspases within the cell death machinery but fail to be activated in response to pro-inflammatory stimuli (Creagh et al., 2003; Taylor et al., 2008). For these experiments, concentrations of caspases-3 and -7 were chosen that achieved robust, but incomplete, proteolysis of their known substrates, RhoGDI2, co-chaperone p23 and XIAP (FIG. 3). These concentrations were chosen to avoid using saturating, non-physiological, amounts of these caspases.

As FIGS. 4 and 5 illustrate, caspases-3 and -7 readily processed both human (SEQ ID NO. 2) and murine (SEQ ID No. 6) IL-33, with caspase-7 being much more efficient in this regard. Importantly, neither of the latter caspases cleaved IL-1β under the same conditions (FIG. 4). Whereas robust IL-33 processing was readily observed at low concentrations (3-7 nM) of caspase-7, caspase-1 failed to cleave IL-33 even at several-fold higher concentrations. Once again, caspase-1 readily processed IL-1β under conditions where it failed to process IL-33 to any significant degree (FIGS. 1 and 4). These data argue that IL-33 is preferentially cleaved by caspases that are activated during apoptosis as opposed to inflammation.

Example 3

Proteolysis of IL-33 in Apoptotic Cell-Free Extracts

To explore IL-33 processing by apoptotic and inflammatory caspases further, we used a well established cell-free system based upon cytosolic extracts derived from LPS-treated monocytic THP-1 cells, where inflammatory caspases can be activated by incubating these extracts at 37° C. (Yamin et al., 1996; Martinon et al., 2002; Martinon et al., 2006). Upon incubation of THP-1 cell-free extracts at 37° C., caspase-1 was processed to its active form and maturation of endogenous IL-1β was readily detected (FIG. 6). As expected, caspase-3 was not activated under these conditions, as indicated by the failure of this protease to undergo proteolytic maturation (FIG. 6). In sharp contrast to the robust processing of IL-1β seen under these conditions, processing of human (SEQ ID NO. 2) or mouse (SEQ ID NO. 6) IL-33 was barely detectable (FIG. 7), again suggesting that IL-33 is a poor substrate for caspase-1 and other inflammatory caspases.

Using the same THP-1 cell-free system, apoptotic caspases can be activated by addition of cytochrome c and dATP to the extracts, as the latter act as co-factors for assembly of the Apaf-1/caspase-9 apoptosome (Li et al., 1997; Slee et al., 1999; Hill et al., 2004). Under these conditions, caspase-1 activation was attenuated and IL-1β proteolysis was much less efficient, whereas caspase-3 was robustly activated (FIG. 6). In contrast to the lack of processing of IL-33 under conditions where inflammatory caspases were activated, this protein was processed very efficiently upon activation of apoptotic caspases through addition of cytochrome c and dATP to the extracts (FIG. 7), again arguing that IL-33 is a preferred substrate for apoptotic as opposed to inflammatory caspases.

We also used a cell-free system based upon cytosolic extracts of Jurkat cells, which are essentially devoid of caspase-1 (Chow et al., 1999). Addition of cytochrome c and dATP to Jurkat extracts resulted in rapid activation of apoptotic caspases and proteolytic processing of multiple caspase substrates (FIG. 8). Proteolysis of human and murine IL-33 was again readily observed under these conditions (FIG. 9). Taken together with our earlier observations made using recombinant caspases (FIGS. 1 to 5), these results strongly suggest that IL-33 is a physiological substrate for caspases activated during apoptosis rather than inflammation.

Example 4

IL-33 is Cleaved at a Single Site that is Conserved Between the Human and Murine Forms of this Cytokine It has been proposed that human IL-33 is proteolytically processed by caspase-1 at Asp110 and that this represents the biologically-active form of this cytokine (Schmitz et al., 2005). However, this site is not conserved between the human (SEQ ID NO. 2) and murine (SEQ ID NO. 6) forms of IL-33, making it highly unlikely that IL-33 is processed at this residue (FIG. 10). To identify the caspase-processing site within IL-33, we inspected the human and mouse IL-33 sequences for conserved tetrapeptide motifs containing Asp residues that may qualify as caspase cleavage motifs. Based upon the approximate molecular weights of the caspase-mediated cleavage products of IL-33 observed in our experiments (FIGS. 4 and 7), a conserved caspase cleavage motif was located at Asp178 within human IL-33 ($^{175}$DGVD$^{178}$ (SEQ ID NO. 10)) and Asp175 within murine IL-33 ($^{172}$DGVD$^{175}$ (SEQ ID NO.11)) that may represent the site of caspase-mediated proteolysis (FIG. 10).

We therefore expressed truncations of human IL-33 corresponding to the putative cleavage products generated through processing at Asp178 (SEQ ID NOS 12 and 13). As can be seen from FIG. 11, these truncated IL-33 proteins displayed precisely the same SDS-PAGE mobilities as full length IL-33 cleaved by caspase-7 (or caspase-3; data not shown). Furthermore, the truncated IL-33 mutants failed to be further processed by caspase-7 (FIG. 11), strongly suggesting that human IL-33 is processed at Asp178 and not Asp110 as previously claimed. We also expressed recombinant full-length GST-IL-33 in bacteria and cleaved this protein with caspase-7 (FIG. 12). The resulting fragments were then analysed using MALDI-TOF mass spectrometry and the peptide coverage of these fragments strongly indicated that the caspase cleavage site was located between amino acids 159 and 187 (FIG. 13), which encompassed the conserved DGVD$^{175/178}$ motif discussed above. Thus, we generated point mutations in human (SEQ ID NOS 3 and 4) and murine (SEQ ID NOS 7 and 8) IL-33 corresponding to the putative caspase cleavage site (Asp178 in human and Asp175 in mouse) and these mutants were completely resistant to processing by any of the caspases examined (FIG. 14). Furthermore, this point mutant was also completely protected from proteolysis in apoptotic Jurkat cell-free extracts under conditions where wild-type IL-33 was completely cleaved (FIG. 15).

Based upon the initial observations of Schmitz et al. (2005), all investigations carried out to date with IL-33 have used an artificially-truncated form of this cytokine, IL-33$^{112-270}$ (SEQ ID NO.14), that was proposed to represent the caspase-cleaved form of this protein. However, our experiments indicate that this form of IL-33 would still contain the actual caspase cleavage site and therefore be susceptible to caspase-mediated proteolysis. To confirm this, we also generated the artificially-truncated form of IL-33 (amino acids 112-270) as well as the D178A mutant form of this truncation. As FIG. 16 clearly indicates, IL-33$^{112-270}$ was cleaved by caspase-7 whereas the IL-33$^{112-270}$ D178A mutant was completely resistant to proteolysis.

These data demonstrate that IL-33 is cleaved by caspase-3 and -7 within a conserved motif at Asp178 in the human form of this cytokine (Asp175 in the mouse). This has important implications, as all previous studies on IL-33 have exclusively used a truncated form of this protein based on a predicted caspase cleavage site (at Asp110) that has failed to be verified by our investigations and is not conserved between human and mouse IL-33.

Example 5

IL-33 is Cleaved During Apoptosis

To confirm that IL-33 is cleaved by apoptotic caspases in a cellular context, we transiently overexpressed FLAG-tagged IL-33 in human HeLa cells and induced these cells to die by exposure to a panel of pro-apoptotic stimuli, including Daunorubicin, TNF and Cisplatin (FIG. 17). Robust processing of IL-33 was observed under conditions where apoptosis was initiated, but importantly, the IL-33$^{D178A}$ point mutant was not cleaved under the same conditions (FIG. 18). Furthermore, inhibition of caspase activation or activity in HeLa cells, through overexpression of Bcl-xL or by inclusion of a poly-caspase inhibitor (z-VAD-fmk) in the medium, also blocked apoptosis-associated proteolysis of IL-33 (FIGS. 19 and 20). Thus, IL-33 is cleaved during apoptosis and this occurs at the same site (Asp178) of caspase-mediated processing of IL-33 in vitro.

Example 6

IL-33 does not Require Proteolytic Processing for Activity

Certain members of the IL-1 family, such as IL-1β require proteolytic processing to convert their inactive precursors into the active cytokines (Mosley et al., 1987a,b; Thornberry et al., 1992). However, other cytokines in this family, such IL-1α, display biological activity whether they are proteolytically processed or not (Mosley et al., 1987a,b). Because all previous studies on IL-33 have used a truncated form of this cytokine that does not represent either the full-length or the bona fide caspase-cleaved form of IL-33 (Schmitz et al., 2005; Allakhverdi et al., 2007; Chackerian et al., 2007; Ali et al., 2007), it is therefore not clear whether proteolysis modulates the activity of this cytokine as the biological activity of full length IL-33 has not been assessed.

To explore the impact of caspase-mediated proteolysis on the biological activity of IL-33, we expressed recombinant full-length GST-IL-33 and incubated this protein with caspase-7 to generate cleaved IL-33 protein (see FIG. 12). Note that a GST-fusion protein was used due to the extreme insolubility of full length untagged IL-33 when expressed in bacterial or yeast expression systems. We then compared the ability of full-length GST-IL-33, versus the caspase-cleaved form of this protein, to promote NFκB activation in a ST2-receptor-dependent manner. For this purpose, we used HEK293T cells transfected with the ST2 receptor along with a NFκB-responsive promoter. As FIG. 21 illustrates, whereas we detected robust NFκB activation in response to the full-length IL-33 protein, the activity of the caspase-cleaved form of this protein was substantially reduced. Similar results were also observed using the artificially-truncated form of IL-33 (amino acids 112-270 (SEQ ID NO. 14)), which also exhibited reduced activity upon caspase-mediated proteolysis. These data suggest, in direct opposition to the prevailing view, that caspase-mediated proteolysis of IL-33 results in a decrease rather than an increase in the activity of this cytokine. Moreover, our data also suggest that full-length IL-33 is biologically active and does not require proteolytic processing for acquisition of ST2-dependent receptor activation.

We also compared the activity of full length GST-IL-33 with the artificially-truncated version of this protein (amino acids 112-270 (SEQ ID NO. 14); FIG. 22) that is currently used by most laboratories as 'mature' IL-33. As FIG. 23 shows IL-33$^{112-270}$ had comparable activity to full-length GST-IL-33 in the ST2-dependent NFκB reporter assay. However, as we have shown above, this truncated form of IL-33 is not the form that would be produced through caspase-dependent proteolysis. Therefore, we also generated recombinant forms of IL-33 equivalent to the caspase-generated cleavage products (IL-33$^{112-178}$ (SEQ ID NO. 15) and IL-33$^{179-270}$ (SEQ ID NO. 13); FIG. 22) to ask whether these fragments could promote ST2-dependent NFκB activation. However, compared to either full length GST-IL-33 or the artificially-truncated IL-33$^{112-270}$ (SEQ ID NO. 14), when expressed independently neither fragment was found to be capable of promoting ST2-dependent NFκB activation (FIG. 23).

Collectively, these data suggest that IL-33 is active as a full-length molecule, or when artificially-truncated after amino acid 111, and that caspase-mediated processing is not required for the production of mature IL-33. These observations are reminiscent of the pattern of activity reported for IL-1α as this cytokine displays biological activity both as a precursor as well as an N-terminally-truncated protein (Mosley et al., 1987a,b). Thus, the proposal that IL-33 is activated through proteolysis by caspase-1 (Schmitz et al., 2005), similar to IL-1β and IL-18, appears unfounded. Indeed, proteolytic processing of full length IL-33 by caspases diminished the activity of this cytokine (FIG. 21), possibly through destabilizing the protein and/or by promoting the separation of IL-33 into fragments that are incapable of promoting efficient ST2 receptor stimulation (FIG. 23).

Example 7

Pro-IL-33 can Bind to the ST2 Receptor

Because the preceding experiments indicated that pro-IL-33 possessed ST2-dependent biological activity, this suggested that full length IL-33 was capable of interacting with the ST2 receptor. To confirm this, we performed in vitro pulldown assays where we incubated sepharose-immobilized full-length GST-IL-33, or caspase-cleaved GST-IL-33, with a soluble Fc-ST2 fusion protein to determine whether both forms of IL-33 bound to the ST2 receptor. As FIG. 24 shows, both forms of GST-IL-33 specifically captured Fc-ST2 in the assay. We also carried out the reciprocal experiment where we immobilized Fc-ST2 on protein A/G agarose and assessed the binding of soluble full-length GST-IL-33 or the caspase-cleaved form of this protein (FIG. 25). Once again, we observed that both the cleaved as well as the full-length forms of GST-IL-33 were able to interact with the ST2 receptor. Because caspase-processed IL-33 was still capable of interacting with the ST2 receptor, this suggests that the loss of biological activity observed (FIG. 21) was unrelated to loss of receptor-binding per se but may be related to other factors. However, it remains possible that the affinity of ST2 receptor binding by the cleaved from of IL-33 may be diminished.

Example 8

IL-33 Stability is Modulated Through Caspase-Mediated Proteolysis

To explore the consequences of caspase-mediated cleavage of IL-33 further, we asked whether caspase-mediated proteolysis might destabilize this cytokine, possibly by opening the molecule up to attack by serum proteases. To test this, we used the serum protease α-chymotrypsin as a probe for IL-33 stability as many cytokines are rapidly inactivated through degradation in the peripheral circulation (Shechter et al., 2001). As FIG. 26 shows, whereas IL-33 was relatively resistant to proteolysis by α-chymotrypsin, pre-treatment of IL-33 with caspase-7 rendered this cytokine much more susceptible to degradation by α-chymotrypsin. Differential susceptibility of the caspase-cleaved form of IL-33, versus the uncleaved form, to α-chymotrypsin-mediated degradation was observed over a wide concentration range (FIGS. 26 and 27). Similar results were also observed in response to proteinase K treatment (FIGS. 28 and 29).

These data indicate that caspase-mediated proteolysis of IL-33 provokes structural changes that render this cytokine substantially more susceptible to serum protease-mediated inactivation. This suggests that rather than abolishing the biological activity of IL-33 (by blocking ST2 receptor binding), caspases may be involved in reducing the half-life of IL-33, by increasing the sensitivity of this cytokine to attack by serum proteases.

Example 9

The Caspase-Cleaved Form of IL-33 Exhibits Diminished Activity In Vivo

To elucidate whether the caspase-cleaved form of IL-33 was also less potent in vivo we then compared the activity of both forms of IL-33 in a mouse model. Mice treated with daily injections of IL-33 (i.p.) over a 6 day period exhibited dramatic increases in splenic weight and cellularity (FIG. 30). Granulocyte numbers in the peritoneal space, the peripheral blood and the spleen were highly elevated (FIGS. 31 to 33), with increases in eosinophil numbers particularly evident (FIGS. 32 and 33). In addition, serum IL-4 and IL-5 levels were dramatically elevated in response to IL-33, as previously reported (FIG. 34). Furthermore, IL-5 and IgA levels were also greatly elevated in the lungs of IL-33-treated mice (FIG. 34). Strikingly, all of these responses were substantially reduced in mice treated with an identical regime of caspase-cleaved IL-33 (FIGS. 30 to 34). Furthermore, whereas restimulation of splenocytes and mesenteric lymph node-derived lymphocytes from IL-33-treated mice resulted in robust IL-5 production, these responses were also diminished in mice treated with caspase-cleaved IL-33 (FIGS. 35A and B). Collectively, these data provide strong support for the idea that caspase-mediated cleavage of IL-33 diminishes, rather than increases, the biological activity of this cytokine.

Example 10

Preparation of Antibodies

Antibodies in accordance with the invention may include:
antibodies that bind to IL-33 and are capable of neutralizing IL-33 biological activity by preventing this cytokine from binding and/or activating the IL-33 receptor(s). Such antibodies may bind at any point along the length of the IL-33 polypeptide (SEQ ID NO. 2).
antibodies that bind in the region of the caspase cleavage site of IL-33. For example antibodies that bind in the region of amino acids 155-198 (SEQ ID NO. 16), or amino acids 165-188 (SEQ ID NO. 17) such as amino acids 175-178 (SEQ ID NO. 10) within the IL-33 polypeptide. The binding of such antibodies may inhibit the activity of IL-33.
antibodies that selectively bind to a protease-cleaved form of IL-33 for example antibodies that bind within the region of amino acids 1-178 (SEQ ID NO. 12) or antibodies that bind within the region of 179-270 (SEQ ID NO. 13) of IL-33. Antibodies that selectively bind to a protease cleaved form of IL-33 may be useful for monitoring apoptosis in IL-33 producing cells and/or tumours. The protease cleaved form of IL-33 may be generated by caspases.
catalytic antibodies that bind in the region of the caspase cleavage site and promote IL-33 proteolysis at this site, thereby attenuating the activity of this cytokine. Such antibodies may bind in the region of amino acids 175-178 (SEQ ID NO. 10) and regions overlapping this region for example antibodies that bind in the region of amino acids 155-198 (SEQ ID NO. 16), or amino acids 165-188 (SEQ ID NO. 17).

Antibodies may be generated using conventional techniques for polyclonal, monoclonal and humanised antibody preparation, for example by immunizing mice, rabbits, goats or another suitable mammalian species, with a suitable immunogen or immunogenic preparation such as peptides derived from specific regions, such as the regions identified above, within IL-33. Peptides can be made more immunogenic by conjugation to KLH or another hapten. Alternatively, the isolated full length IL-33 polypeptide, or truncations of this polypeptide, for example the products obtained by protease cleavage of IL-33, can be used as the immunogen to generate antibodies to this protein.

Any fragment of the IL-33 protein which contains at least one antigenic determinant may be used to generate antibodies. The antigenic peptide of IL-33 comprises at least 4 consecutive amino acid residues of the IL-33 polypeptide sequence and encompasses an epitope of IL-33 such that an antibody raised against the peptide forms a specific immune complex with IL-33. The antigenic peptide may comprise at least 10 amino acid residues, for example at least 15 amino acid residues, such as at least 20 amino acid residues, or at least 30 amino acid residues. The antigenic peptide may be any one of the peptide sequences of SEQ ID NO. 2, SEQ ID NO. 6, SEQ ID NO. 9, SEQ ID NO. 10, SEQ ID NO. 11, SEQ ID NO. 12, SEQ ID NO. 13, SEQ ID NO. 14, SEQ ID NO. 15, SEQ ID NO. 16 and SEQ ID NO. 17 or antigenic fragments or portions thereof.

Preferred epitopes encompassed by the antigenic peptide include regions of IL-33 that span the caspase cleavage site of IL-33 for example peptides that include amino acid residues 175 to 178 such as SEQ ID NO. 10, SEQ ID NO. 17 and SEQ ID NO. 16.

A suitable immunogenic preparation can contain, for example, recombinantly expressed IL-33 protein or a chemically synthesized IL-33 polypeptide. The preparation can further include an adjuvant, such as Freund's complete or incomplete adjuvant, or similar immunostimulatory agent. Immunisation of a suitable mammal, such as a rabbit or goat, with an immunogenic IL-33 preparation induces a polyclonal anti-IL-33 antibody response.

The term "antibody" as used herein refers to immunoglobulin molecules and immunologically active portions of immunoglobulin molecules, i.e., molecules that contain an antigen binding site which specifically binds (immunoreacts with) an antigen, such as IL-33. Examples of immunologically active portions of immunoglobulin molecules include F(ab) and F(ab')2 fragments which can be generated by treating the antibody with an enzyme such as pepsin. The invention provides polyclonal and monoclonal antibodies that bind IL-33. The term "monoclonal antibody" as used herein, refers to a population of antibody molecules that contain only one species of an antigen binding site capable of immunoreacting with a particular epitope of IL-33. A monoclonal antibody composition thus typically displays a single binding affinity for a particular IL-33 peptide or polypeptide with which it immunoreacts.

The invention also provides antibody compositions, either polyclonal or monoclonal, which are capable of selectively binding to an epitope-containing a polypeptide comprising a contiguous span of at least 4 amino acids. The invention also provides a purified or isolated antibody capable of specifically binding to the full length IL-33 protein or to fragments thereof, such as fragments generated by caspase cleavage of IL-33, containing an epitope against which antibodies were generated.

Polyclonal antibodies can be prepared as described above by immunizing a suitable subject with an IL-33 immunogen. The IL-33 antibody titer in the immunised subject can be monitored over time by standard techniques, such as with an enzyme linked immunosorbent assay (ELISA) using immobilized IL-33. If desired, the antibody molecules directed against IL-33 can be isolated from the mammal (e.g., from the blood) and further purified by well known techniques, such as protein A chromatography to obtain the IgG fraction. At an appropriate time after immunisation, e.g., when the anti-IL-33 antibody titers are highest, antibody-producing cells can be obtained from the subject and used to prepare monoclonal antibodies by standard techniques, such as those described in the following references: the hybridoma technique originally described by Kohler and Milstein (1975) Nature 256:495-497) (see also, Brown et al. (1981) J. Immunol. 127:539-46; Brown et al. (1980) J. Biol. Chem. 255:4980-83; Yeh et al. (1976) PNAS 76:2927-31), the human B cell hybridoma technique (Kozbor et al. (1983) Immunol Today 4:72), the EBV-hybridoma technique, Monoclonal Antibodies and Cancer Therapy, or trioma techniques. The technology for producing monoclonal antibody hybridomas is well known (see generally Roitt's Essential Immunology, 11$^{th}$ Edition, Blackwell Scientific (2006) Chapter 6, pages 111-118). Briefly, an immortal cell line (typically a myeloma) is fused to lymphocytes (typically splenocytes) from a mammal immunized with an IL-33 immunogen as described above, and the culture supernatants of resulting hybridoma cells are screened to identify a hybridoma producing a monoclonal antibody that binds IL-33.

Any of the many well known protocols used for fusing lymphocytes and immortalized cell lines can be applied for the purpose of generating an anti-IL-33 monoclonal antibody (see, e.g., G. Galfre et al. (1977) Nature 266:55052). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from American Type Culture Collection (ATCC). Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind IL-33, e.g., using a standard ELISA assay.

Alternatively to preparing monoclonal antibody-secreting hybridomas, a monoclonal anti-IL-33 antibody can be identified and isolated by screening a recombinant combinatorial immunoglobulin library (e.g., an antibody phage display library) with IL-33 to thereby isolate immunoglobulin library members that bind IL-33. Kits for generating and screening phage display libraries are commercially available for example, from Pharmacia and Stratagene. Additionally, examples of methods and reagents particularly amenable for use in generating and screening antibody display library can be found in, for example, Fuchs et al. (1991) Bio/Technology 9:1370-1372; Huse et al. (1989) Science 246:1275-1281; Griffiths et al. (1993) EMBO J. 12:725-734; Hawkins et al. (1992) J. Mol. Biol. 226:889-896; Clarkson et al. (1991) Nature 352:624-628; Gram et al. (1992) PNAS 89:3576-3580; Hoogenboom et al. (1991) Nuc. Acid Res. 19:4133-4137; Barbas et al. (1991) PNAS 88:7978-7982; and McCafferty et al. Nature (1990) 348:552-554.

Additionally, recombinant anti-IL-33 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Better et al. (1988) Science 240:1041-1043; Liu et al. (1987) PNAS 84:3439-3443; Liu et al. (1987) J. Immunol. 139:3521-3526; Sun et al. (1987) PNAS 84:214-218; Nishimura et al. (1987) Canc. Res. 47:999-1005; Wood et al. (1985) Nature 314:446-449; and Shaw et al. (1988) J. Natl. Cancer Inst. 80:1553-1559); Morrison, S. L. (1985) Science 229:1202-1207; Jones et al. (1986) Nature 321:552-525; Verhoeyan et al. (1988) Science 239:1534; and Beidler et al. (1988) J. Immunol. 141:4053-4060.

Monoclonal anti-IL-33 antibody can be used to isolate IL-33 by standard techniques, such as affinity chromatography or immunoprecipitation. An anti-IL-33 antibody can facilitate the purification of natural M-33 from cells and of recombinantly produced IL-33 expressed in host cells. Moreover, an anti-IL-33 antibody can be used to detect IL-33 protein (e.g., in a cellular lysate or cell supernatant) in order to evaluate the abundance and pattern of expression of the IL-33 protein. Anti-IL-33 antibodies can be used for the detection of apoptosis for example, antibodies raised to the cleaved forms of IL-33 (for example SEQ ID NO. 12 and/or SEQ ID NO. 13) may be useful in monitoring cells obtained from a solid tumour of a patient undergoing chemotherapy treatment to assess whether the chemotherapy treatment is working. The presence of cleaved forms of IL-33 in cells acts as a marker of apoptosis and can be used to determine whether the chemotherapy treatment regime is effective. Anti-IL-33 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125 I, 131 I, 35 S or 3H.

IL-33 antibodies could be used for the targeted delivery of compounds and/or molecules and/or enzymes, for example the targeted delivery of an enzyme capable of cleaving IL-33. The enzyme may be a protease such as trypsin or thrombin or caspase or another common protease. The caspase may be any one of caspase-1, caspase-2, caspase-3, caspase-4, caspase-5, caspase-6, caspase-7, caspase-8, caspase-9, caspase-10 and caspase-14. The caspase may be caspase-3 or caspase-7.

Example 11

Immunoconjugates

The invention provides anti-IL-33 antibody immunoconjugates, where anti-IL-33 antibodies (whether neutralizing or not) are chemically-coupled to a protease capable of cleaving IL-33 between amino acids 178 and 179 (SEQ ID NO. 10). Such anti-IL-33 antibody/protease conjugates may be considerably more potent as neutralizing agents than anti-IL-33 antibodies alone. In one embodiment, the protease conjugated to an anti-IL-33 antibody may be a caspase for example any one of the caspases selected from: caspase-1, caspase-2, caspase-3, caspase-4, caspase-5, caspase-6, caspase-7, caspase-8; caspase-9, caspase-10, or caspase-14. In one embodiment the caspase may be selected from caspase-3 or caspase-7. It is envisaged that proteases such as trypsin, thrombin, or additional common proteases could also be delivered to IL-33, by conjugating these proteases to anti-IL-33 antibodies, for the purposes of cleaving IL-33 and attenuating its activity.

Antibody conjugates can be generated using chemical crosslinking agents such, as Succinimidyl-4-(maleimidomethyl)cyclohexane-1-carboxylate (SMCC) which is a non-cleavable and membrane permeable crosslinker. SMCC contains an amine-reactive N-hydroxysuccinimide (NHS ester) and a sulfhydryl-reactive maleimide group. NHS esters react with primary amines at pH 7-9 to form stable amide bonds. Maleimides react with sulfhydryl groups at pH 6.5-7.5 to form stable thioether bonds. In this type of conjugation, the NHS ester is reacted first with the antibody, excess crosslinking reagent removed and then the sulfhydryl-containing enzyme molecule is added. This two-step reaction scheme results in formation of specific antibody-enzyme conjugates.

Commercially available conjugation kits can be obtained, for example, from Pierce Biotechnology. Antibody conjugates can be generated using standard conjugation techniques that are know in the art, for example using the methods described in Bieniarz, C., et al. (1996) Extended length Heterobifunctional Coupling Agents for Protein Conjugations. Bioconjug. Chem. 7, 88-95; Brinkley, M. A. (1992) A survey of methods for preparing protein conjugates with dyes, haptens and crosslinking reagents. Bioconjugate Chem. 3, 2-13; and Uto, I., Ishimatsu, T., Hirayama, H., Ueda, S., Tsuruta, J. and Kambara, T. (1991). Determination of urinary Tamm-Horsfall protein by ELISA using a maleimide method for enzyme-antibody conjugation. J. Immunol. Methods 138, 87-94.

In an alternative embodiment, conjugates of soluble IL-33 receptor (ST2/T1) and proteases may be formed such that circulating IL-33 may be neutralized through binding to the soluble IL-33 receptor molecule followed by proteolysis of the bound IL-33 by the protease conjugated to soluble IL-33 receptor. Such IL-33 receptor-protease conjugates may be considerably more potent as neutralizing agents than soluble IL-33 receptor alone. In one embodiment, the protease conjugated to soluble IL-33 receptor (ST2/T1) may be a caspase for example any one of the caspases selected from: caspase-1, caspase-2, caspase-3, caspase-4, caspase-5, caspase-6, caspase-7, caspase-8, caspase-9, caspase-10, or caspase-14. In one embodiment the caspase may be selected from caspase-3 or caspase-7. It is envisaged that proteases such as trypsin, thrombin, or additional common proteases could also be delivered to IL-33, by conjugating these proteases to soluble IL-33 receptor (ST2/T1), for the purposes of cleaving this protein and attenuating its activity. Soluble IL-33 receptor may be generated through fusion of the gene sequence encoding the extracellular portion of this receptor, or a natural alternatively-spliced form of this receptor, to the Fc coding portion of immunoglobulin to create an IL-33 receptor-Fc fusion protein.

Conjugates of soluble IL-33 receptor (ST2/T1) and proteases can be generated using chemical crosslinking agents such as Succinimidyl-4-(maleimidomethyl)cyclohexane-1-carboxylate (SMCC) which is a non-cleavable and membrane permeable crosslinker. SMCC contains an amine-reactive N-hydroxysuccinimide (NHS ester) and a sulfhydryl-reactive maleimide group. NHS esters react with primary amines at pH 7-9 to form stable amide bonds. Maleimides react with sulfhydryl groups at pH 6.5-7.5 to form stable thioether bonds.

Commercially available conjugation kits can be obtained, for example, from Pierce Biotechnology. Conjugates of soluble IL-33 receptor (ST2/T1) and proteases can be generated using standard conjugation techniques that are know in the art, for example using the methods described in Bieniarz, C., et al. (1996) Extended length Heterobifunctional Coupling Agents for Protein Conjugations. Bioconjug. Chem. 7, 88-95; Brinkley, M. A. (1992) A survey of methods for preparing protein conjugates with dyes, haptens and crosslinking reagents. Bioconjugate Chem. 3, 2-13; and Uto, I., Ishimatsu, T., Hirayama, H., Ueda, S., Tsuruta, J. and Kambara, T. (1991).

Example 12

Method of Screening Compounds/Other Molecules that Alter the Activity of IL-33

The invention provides a method for screening for compounds or other molecules that can interact with IL-33 within the region of amino acids 175-178 (SEQ ID NO. 10), or within the region spanning, amino acids 175 to 178 such as the region specified by amino acids 165-188 (SEQ ID NO. 17), or amino acids 155-198 (SEQ ID NO. 16) for the purposes of attenuating or neutralizing the biological activity of IL-33.

The invention further provides for a method for screening of compounds or enzymes that inhibit the biological activity of IL-33 by binding and/or cleaving this protein within the region of amino acids 175-178 (SEQ ID NO. 10), or within the region spanning amino acids 175 to 178 such as the region specified by amino acids 165-188 (SEQ ID NO. 17), or amino acids 155-198 (SEQ ID NO. 16).

Conventional screening methods, such as high throughput screening methods may be used to screen compounds and/or other molecules in accordance with the invention.

The screening assay may be in vitro method for identifying compounds and/or molecules suitable for modifying the biological activity of IL-33 comprising the steps of:
(a) contacting an IL-33 polypeptide with a compound and/or a molecule to be tested;
(b) assaying the activity of IL-33 in the presence of said compound and/or molecule; and
(c) comparing the level of IL-33 activity from step (b) to the level of IL-33 activity in the absence of said compound and/or molecule.

The screening assay may be a biological assay based on HEK293T cells transfected with the ST2 receptor along with a NFκB-responsive promoter. The transfected HEK293T cells may be incubated in the presence or absence of compounds or other molecules that are being tested. Compounds or other molecules that inhibit the ability of IL-33 to induce NFκB responses that are ST2 dependent can be identified by assessing the level of NFκB activation. The presence of full length (uncleaved) IL-33 activates NFκB whereas the presence of cleaved IL-33 reduces NFκB activity.

Example 13

Method for Inhibiting the Activity of IL-33

The invention also provides a method to inhibit the activity of IL-33 by introducing a caspase capable of cleaving IL-33 into an IL-33 producing cell. The caspase may be capable of cleaving IL-33 within the region of amino acids 175-178 (SEQ ID NO. 10) to attenuate the biological activity IL-33. In one embodiment, the caspase so delivered to IL-33-producing cells may be any one of the caspases selected from: caspase-1, caspase-2, caspase-3, caspase-4, caspase-5, caspase-6, caspase-7, caspase-8, caspase-9, caspase-10, or caspase-14. In one embodiment the caspase may be selected from caspase-3 or caspase-7. Delivery of caspases can be achieved through gene delivery vectors, such as viral gene delivery vectors, engineered to express the desired caspase gene.

The technique of using gene delivery vectors is known in the art. Conventional viral gene delivery systems are commercially available, for example suitable viral gene delivery systems include Lentiviral gene delivery vectors, such as those based on pCDH1 and pCDH2 vectors (available from Systembiosciences). The gene delivery vector can be packaged in a suitable packaging cell line (such as 293TN cells) by co-transfecting the pCDH1 or pCDH2 vector containing the gene of interest (for example a caspase) along with pPACK-H1 plasmid mixture (System Biosciences). Recombinant viral particles containing the gene to be delivered are then harvested from 1-3 days after transfection of the packaging cell line. Viral particles can then be purified further by ultracentrifugation.

Example 14

Generation of Mutant Forms of IL-33

In another aspect of the invention there is provided for a modified form of IL-33. The Aspartate at residue 178 can be mutated to any other amino acid with the exception of proline to render the IL-33 polypeptide resistant to caspase-mediated proteolysis. Such modified IL-33 protein is envisaged to be more stable in vivo and exhibit greater biological potency as a result. Such mutant forms of IL-33 can be generated using standard mutagenesis methods where the codon specifying Aspartate position 178 of the human IL-33 gene coding sequence is altered to code for the desired amino acid.

Standard site directed mutagenesis protocols are known in the art. Commercially available site directed mutagenesis kits, for example the Quikchange® kit from Stratagene, can be used to alter the aspartate residue at position 178.

Example 15

Inhibitory RNA

It is envisaged that the activity of IL-33 may also be altered through the use of Small inhibitory RNA (siRNA) molecules that are specifically designed to target the protease cleavage region of IL-33. The siRNA may be of a suitable length to attenuate IL-33 activity for example by preventing the binding of IL-33 to the IL-33 receptor or by neutralising the activity of IL-33. In some embodiments the siRNA molecules may be between 19 and 23 nucleotides in length. The siRNA molecules may comprise a double stranded molecule consisting of a sense and anti-sense strand that are complimentary. The siRNA molecule may correspond to a portion of the gene encoding the protease cleavage site of IL-33 for example a portion of the gene that encodes the amino acid sequence of any one of SEQ ID NO. 16, SEQ ID NO. 17 and SEQ ID NO. 10. Suitable siRNA molecules can be synthesised using conventional techniques know to a person skilled in the art. It is envisaged that siRNA molecules of the invention may be used as antagonists of IL-33 activity.

The invention is not limited to the embodiment hereinbefore described, with reference to the accompanying drawings, which may be varied in construction and detail.

REFERENCES

Ali, S., Huber, M., Kollewe, C., Bischoff, S. C., Falk, W., Martin, M. U. (2007). IL-1 receptor accessory protein is essential for IL-33-induced activation of T lymphocytes and mast cells. Proc Natl Acad Sci USA 104, 18660-5.

Allakhverdi, Z., Smith, D. E., Comeau, M. R., and Delespesse, G. (2007). Cutting Edge: The ST2 ligand IL-33 potently activates and drives maturation of human mast cells. J Immunol 179, 2051-4.

Barbas et al. (1991) PNAS 88:7978-7982

Beidler et al. (1988) J. Immunol. 141:4053-4060.

Better et al. (1988) Science 240:1041-1043

Bieniarz, C., et al. (1996). Extended length Heterobifunctional Coupling Agents for Protein Conjugations. Bioconjug. Chem. 7, 88-95

Brinkley, M. A. (1992). A survey of methods for preparing protein conjugates with dyes, haptens and crosslinking reagents. Bioconjugate Chem. 3, 2-13

Brint, E. K., Xu, D., Liu, H., Dunne, A., McKenzie, A. N., O'Neill, L. A., and Liew, F. Y. (2004). ST2 is an inhibitor of interleukin 1 receptor and Toll-like receptor 4 signaling and maintains endotoxin tolerance. Nat Immunol 5, 373-9.

Brown et al. (1980) J. Biol. Chem. 255:4980-83

Brown et al. (1981) J. Immunol. 127:539-46

Carriere, V., Roussel, L., Ortega, N., Lacorre, D. A., Americh, L., Aguilar, L., Bouche, G., and Girard, J. P. (2007). IL-33, the IL-1-like cytokine ligand for ST2 receptor, is a chromatin-associated nuclear factor in vivo. Proc Natl Acad Sci USA 104, 282-7.

Chackerian, A. A., Oldham, Murphy, E. E., Schmitz, J., Pflanz, S., and Kastelein, R. A. (2007). IL-1 receptor accessory protein and ST2 comprise the IL-33 receptor complex. J Immunol 179, 2551-5.

Chow, S. C., Slee, E. A., MacFarlane, M., and Cohen, G. M. (1999). Caspase-1 is not involved in CD95/Fas-induced apoptosis in Jurkat T cells. Exp Cell Res 246, 491-500.

Clarkson et al. (1991) Nature 352:624-628

Creagh, E. M., Conroy, H., and Martin, S. J. (2003). Caspase-activation pathways in apoptosis and immunity. Immunol Rev 193, 10-21.

Fuchs et al. (1991) Bio/Technology 9:1370-1372

Galfre et al. (1977) Nature 266:55052

Ghayur, T., Banerjee, S., Hugunin, M., Butler, D., Herzog, L., Carter, A., Quintal, L., Sekut, L., Talanian, R., Paskind, M., et al. (1997). Caspase-1 processes IFN-gamma-inducing factor and regulates LPS-induced IFN-gamma production. Nature 386, 619-23.

Gram et al. (1992) PNAS 89:3576-3580

Griffiths et al. (1993) EMBO J. 12:725-734

Gu, Y., Kuida, K., Tsutsui, H., Ku, G., Hsiao, K., Fleming, M. A., Hayashi, N., Higashino, K., Okamura, H., Nakanishi, K., et al. (1997). Activation of interferon-gamma inducing factor mediated by interleukin-1 beta converting enzyme. Science 275, 206-9.

Hawkins et al. (1992) J. Mol. Biol. 226:889-896

Hill, M. M., Adrain, C., Duriez, Creagh, E. M., Martin, S. J. (2004). Analysis of the composition, assembly kinetics and activity of native Apaf-1 apoptosomes. EMBO J. 23, 2134-45.

Kroemer, G., Martin, S. J. (2005). Caspase-independent cell death. Nat Med. 11, 725-30

Hoogenboom et al. (1991) Nuc. Acid Res. 19:4133-4137

Huse et al. (1989) Science 246:1275-1281

Jones et al. (1986) Nature 321:552-525

Kohler and Milstein (1975) Nature 256:495-497

Kozbor et al. (1983) Immunol Today 4:72

Kuida, K., Lippke, J. A., Ku, G., Harding, M. W., Livingston, D. J., Su, M. S., and Flavell, R. A. (1995). Altered cytokine export and apoptosis in mice deficient in interleukin-1 beta converting enzyme. Science 267, 2000-3.

Lavelle, E. C., Grant, G., Pusztai, A., Pfuller, U., O'Hagan, D. T. (2001). The identification of plant lectins with mucosal adjuvant activity. Immunology 102, 77-86

Li, P., Allen, H., Banerjee, S., Franklin, S., Herzog, L., Johnston, C., McDowell, J., Paskind, M., Rodman, L., Salfeld, J. (1995). Mice deficient in IL-1 beta-converting enzyme are defective in production of mature IL-1 beta and resistant to endotoxic shock. Cell 80, 401-11.

Li, P., Nijhawan, D., Budihardjo, I., Srinivasula, S. M., Ahmad, M., Alnemri, E. S., and Wang, X. (1997). Cytochrome c and dATP-dependent formation of Apaf-1/caspase-9 complex initiates an apoptotic protease cascade. Cell 91, 479-89.

Liu et al. (1987) PNAS 84:3439-3443

Liu et al. (1987) J. Immunol. 139:3521-3526

Lohning, M., Stroehmann, A., Coyle, A. J., Grogan, J. L., Lin, S., Gutierrez-Ramos, J. C., Levinson, D., Radbruch, A., and Kamradt, T. (1998). T1/ST2 is preferentially expressed on murine Th2 cells, independent of interleukin 4, interleukin 5, and interleukin 10, and important for Th2 effector function. Proc Natl Acad Sci USA 95, 6930-5.

Maier, J. A., Statuto, M., Ragnotti, G. (1994). Endogenous interleukin 1 alpha must be transported to the nucleus to exert its activity in human endothelial cells. Mol Cell Biol. 14, 1845-51.

Martinon, F., Burns, K., and Tschopp, J. (2002). The inflammasome: a molecular platform triggering activation of inflammatory caspases and processing of proIL-beta. Mol Cell 10, 417-26.

Martinon, F., Petrilli, V., Mayor, A., Tardivel, A., and Tschopp, J. (2006). Gout-associated uric acid crystals activate the NALP3 inflammasome. Nature 440, 237-41.

Martinon, F., and Tschopp, J. (2004). Inflammatory caspases: linking an intracellular innate immune system to autoinflammatory diseases. Cell 117, 561-74.

McCafferty et al. Nature (1990) 348:552-554.

Meisel, C., Bonhagen, K., Lohning, M., Coyle, A. J., Gutierrez-Ramos, J. C., Radbruch, A., and Kamradt, T. (2001). Regulation and function of T1/ST2 expression on CD4+ T cells: induction of type 2 cytokine production by T1/ST2 cross-linking. J Immunol 166, 3143-50.

Morrison, S. L. (1985) Science 229:1202-1207

Mosley, B., Dower, S. K., Gillis, S., Cosman, D. (1987a). Determination of the minimum polypeptide lengths of the functionally active sites of human interleukins 1 alpha and 1 beta. Proc Natl Acad Sci USA 84, 4572-6.

Mosley, B., Urdal, D. L., Prickett, K. S., Larsen, A., Cosman, D., Conlon, P. J., Gillis, S., Dower, S. K. (1987b). The interleukin-1 receptor binds the human interleukin-1 alpha precursor but not the interleukin-1 beta precursor. J. Biol. Chem. 262, 2941-4.

Murphy, B. M., O'Neill, A. J., Adrain, C., Watson, R. W., and Martin, S. J. (2003). The apoptosome pathway to caspase activation in primary human neutrophils exhibits dramatically reduced requirements for cytochrome C. J. Exp. Med. 197, 625-32.

Nishimura et al. (1987) Canc. Res. 47:999-1005

Patel, V. A., Longacre-Antoni, A., Cvetanovic, M., Lee, D. J., Feng, L., Fan, H., Rauch, J., Ucker, D. S., and Levine, J. S. (2007). The affirmative response of the innate immune system to apoptotic cells. Autoimmunity 40, 274-80.

Roitt's Essential Immunology, 11$^{th}$ Edition, Blackwell Scientific (2006) Chapter 6, pages 111-118

Scaffidi, P., Misteli, T., Bianchi, M. E. (2002). Release Of chromatin protein HMGB1 by necrotic cells triggers inflammation. Nature 418, 191-5.

Schmitz, J., Owyang, A., Oldham, E., Song, Y., Murphy, E., McClanahan, T. K., Zurawski, G., Moshrefi, M., Qin, J., Li, X., et al. (2005). IL-33, an interleukin-1-like cytokine that signals via the IL-1 receptor-related protein ST2 and induces T helper type 2-associated cytokines. Immunity 23, 479-90.

Shaw et al. (1988) J. Natl. Cancer Inst. 80:1553-1559)

Shechter, Y., Preciado-Patt, L., Schreiber, G., Fridkin, M. (2001). Prolonging the half-life of human interferon-alpha 2 in circulation: Design, preparation, and analysis of (2-sulfo-9-fluorenylmethoxycarbonyl)-7-interferon-alpha 2. Proc Natl Acad Sci U S A. 98, 1212-7.

Slee, E. A., Harte, M. T., Kluck, R. M., Wolf, B. B., Casiano, C. A., Newmeyer, D. D., Wang, H. G., Reed, J. C., Nicholson, D. W., Alnemri, E. S., et al. (1999). Ordering the cytochrome c-initiated caspase cascade: hierarchical activation of caspases-2, -3, -6, -7, -8, and -10 in a caspase-9-dependent manner. J Cell Biol 144, 281-92.

Sun et al. (1987) PNAS 84:214-218

Taylor R C, Cullen S P, Martin S J. (2008). Apoptosis: controlled demolition at the cellular level. Nat Rev Mol Cell Biol. 9, 231-41.

Thornberry, N. A., Bull, H. G., Calaycay, J. R., Chapman, K. T., Howard, A. D., Kostura, M. J., Miller, D. K., Molineaux, S. M., Weidner, J. R., Aunins, J., et al. (1992). A novel heterodimeric cysteine protease is required for interleukin-1 beta processing in monocytes. Nature 356, 768-74.

Townsend, M. J., Fallon, P. G., Matthews, D. J., Jolin, H. E., and McKenzie, A. N. (2000). T1/ST2-deficient mice demonstrate the importance of T1/ST2 in developing primary T helper cell type 2 responses. J Exp Med 191, 1069-76.

Uto, I., Ishimatsu, T., Hirayama, H., Ueda, S., Tsuruta, J. and Kambara, T. (1991). Determination of urinary Tamm-Horsfall protein by ELISA using a maleimide method for enzyme-antibody conjugation. J. Immunol. Methods 138, 87-94

Verhoeyan et al. (1988) Science 239:1534

Voll, R. E., Herrmann, M., Roth, E. A., Stach, C., Kalden, J. R., and Girkontaite, I. (1997). Immunosuppressive effects of apoptotic cells. Nature 390, 350-351.

Wood et al. (1985) Nature 314:446-449

Xu, D., Chan, W. L., Leung, B. P., Huang, F., Wheeler, R., Piedrafita, D., Robinson, J. H., and Liew, F. Y. (1998). Selective expression of a stable cell surface molecule on type 2 but not type 1 helper T cells. J Exp Med 187, 787-94.

Yamin, T. T., Ayala, J. M., and Miller, D. K. (1996). Activation of the native 45-kDa precursor form of interleukin-1-converting enzyme. J Biol Chem 271, 13273-82.

Yeh et al. (1976) PNAS 76:2927-31

---

The invention claimed is:

1. An isolated IL-33 polypeptide that is resistant to caspase mediated cleavage said polypeptide comprising the amino acid sequence set forth in SEQ ID NO:4.

2. The isolated IL-33 polypeptide as claimed in claim 1 wherein the IL-33 polypeptide has been modified in vitro to make it resistant to caspase cleavage.

3. The isolated IL-33 polypeptide as claimed in claim 2 wherein the caspase cleavage site has been mutated.

4. The isolated IL-33 polypeptide as claimed in claim 1 wherein the polypeptide is resistant to cleavage by caspase-7.

5. The isolates IL-33 polypeptide as claimed in claim 1 wherein the polypeptide is resistant to cleavage by caspase-3.

6. The isolated IL-33 polypeptide as claimed in claim 1 wherein the polypeptide is resistant to cleavage by caspase-7 and caspase-3.

* * * * *

SEQUENCE LISTING

<160> NUMBER OF SEQ ID NOS: 17

<210> SEQ ID NO 1
<211> LENGTH: 813
<212> TYPE: DNA
<213> ORGANISM: homo sapiens

<400> SEQUENCE: 1

```
atgaagccta aaatgaagta ttcaaccaac aaaatttcca cagcaaagtg gaagaacaca      60
gcaagcaaag ccttgtgttt caagctggga aaatcccaac agaaggccaa agaagtttgc     120
cccatgtact ttatgaagct ccgctctggc cttatgataa aaaaggaggc ctgttacttt     180
aggagagaaa ccaccaaaag gccttcactg aaaacaggta gaaagcacaa aagacatctg     240
gtactcgctg cctgtcaaca gcagtctact gtggagtgct ttgcctttgg tatatcaggg     300
gtccagaaat atactagagc acttcatgat tcaagtatca caggaatttc acctattaca     360
gagtatcttg cttctctaag cacatacaat gatcaatcca ttactttgc tttggaggat     420 gaaagttatg agatatatgt tgaagacttg aaaaagatg aaaagaaaga taaggtgtta     480
ctgagttact atgagtctca acaccctca aatgaatcag gtgacggtgt tgatggtaag     540
atgttaatgg taaccctgag tcctacaaaa gacttctggt tgcatgccaa caacaaggaa     600
cactctgtgg agctccataa gtgtgaaaaa ccactgccag accaggcctt ctttgtcctt     660
cataatatgc actccaactg tgtttcattt gaatgcaaga ctgatcctgg agtgtttata     720
ggtgtaaagg ataatcatct tgctctgatt aaagtagact cttctgagaa tttgtgtact     780
gaaaatatct tgtttaagct ctctgaaact tag                                  813
```

<210> SEQ ID NO 2
<211> LENGTH: 270
<212> TYPE: PRT
<213> ORGANISM: Homo sapiens

<400> SEQUENCE: 2

```
Met Lys Pro Lys Met Lys Tyr Ser Thr Asn Lys Ile Ser Thr Ala Lys
1               5                  10                   15

Trp Lys Asn Thr Ala Ser Lys Ala Leu Cys Phe Lys Leu Gly Lys Ser
            20                  25                   30

Gln Gln Lys Ala Lys Gly Val Cys Pro Met Tyr Phe Met Lys Leu Arg
        35                  40                   45

Ser Gly Leu Met Ile Lys Lys Glu Ala Cys Tyr Phe Arg Arg Glu Thr
    50                  55                   60

Thr Lys Arg Pro Ser Leu Lys Thr Gly Arg Lys His Lys Arg His Leu
65                  70                  75                   80

Val Leu Ala Ala Cys Gln Gln Gln Ser Thr Val Glu Cys Phe Ala Phe
```

```
                    85                  90                  95
Gly Ile Ser Gly Val Gln Lys Tyr Thr Arg Ala Leu His Asp Ser Ser
                100                 105                 110

Ile Thr Gly Ile Ser Pro Ile Thr Glu Tyr Leu Ala Ser Leu Ser Thr
            115                 120                 125

Tyr Asn Asp Gln Ser Ile Thr Phe Ala Leu Glu Asp Glu Ser Tyr Glu
        130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
            180                 185                 190

Trp Leu His Ala Asn Asn Lys Glu His Ser Val Glu Leu His Lys Cys
        195                 200                 205

Glu Lys Pro Leu Pro Asp Gln Ala Phe Phe Val Leu His Asn Met His
    210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
            260                 265                 270

<210> SEQ ID NO 3
<211> LENGTH: 813
<212> TYPE: DNA
<213> ORGANISM: Homo sapiens

<400> SEQUENCE: 3
atgaagccta aaatgaagta ttcaaccaac aaaatttcca cagcaaagtg gaagaacaca      60
gcaagcaaag ccttgtgttt caagctggga aaatcccaac agaaggccaa agaagtttgc     120
cccatgtact ttatgaagct ccgctctggc cttatgataa aaaaggaggc ctgttacttt     180
aggagagaaa ccaccaaaag gccttcactg aaaacaggta gaaagcacaa aagacatctg     240
gtactcgctg cctgtcaaca gcagtctact gtggagtgct ttgcctttgg tatatcaggg     300
gtccagaaat atactagagc acttcatgat tcaagtatca caggaatttc acctattaca     360
gagtatcttg cttctctaag cacatacaat gatcaatcca ttactttttgc tttggaggat     420 gaaagttatg agatatatgt tgaagacttg aaaaagatg aaaagaaaga taaggtgtta     480
ctgagttact atgagtctca acacccctca aatgaatcag gtgacggtgt tgctggtaag     540
atgttaatgg taaccctgag tcctacaaaa gacttctggt tgcatgccaa caacaaggaa     600
cactctgtgg agctccataa gtgtgaaaaa ccactgccag accaggcctt ctttgtcctt     660
cataatatgc actccaactg tgtttcattt gaatgcaaga ctgatcctgg agtgtttata     720
ggtgtaaagg ataatcatct tgctctgatt aaagtagact cttctgagaa tttgtgtact     780
gaaaatatct tgtttaagct ctctgaaact tag                                  813

<210> SEQ ID NO 4
<211> LENGTH: 270
<212> TYPE: PRT
<213> ORGANISM: Homo sapiens

<400> SEQUENCE: 4

Met Lys Pro Lys Met Lys Tyr Ser Thr Asn Lys Ile Ser Thr Ala Lys
```

```
        1               5                  10                 15
Trp Lys Asn Thr Ala Ser Lys Ala Leu Cys Phe Lys Leu Gly Lys Ser
                20                 25                 30

Gln Gln Lys Ala Lys Gly Val Cys Pro Met Tyr Phe Met Lys Leu Arg
            35                 40                 45

Ser Gly Leu Met Ile Lys Lys Glu Ala Cys Tyr Phe Arg Arg Glu Thr
        50                 55                 60

Thr Lys Arg Pro Ser Leu Lys Thr Gly Arg Lys His Lys Arg His Leu
65                  70                 75                  80

Val Leu Ala Ala Cys Gln Gln Gln Ser Thr Val Glu Cys Phe Ala Phe
                85                 90                 95

Gly Ile Ser Gly Val Gln Lys Tyr Thr Arg Ala Leu His Asp Ser Ser
            100                105                110

Ile Thr Gly Ile Ser Pro Ile Thr Glu Tyr Leu Ala Ser Leu Ser Thr
        115                120                125

Tyr Asn Asp Gln Ser Ile Thr Phe Ala Leu Glu Asp Glu Ser Tyr Glu
        130                135                140

Ile Tyr Val Glu Asp Leu Lys Lys Asp Glu Lys Lys Asp Lys Val Leu
145                150                155                 160

Leu Ser Tyr Tyr Glu Ser Gln His Pro Ser Asn Glu Ser Gly Asp Gly
                165                170                175

Val Ala Gly Lys Met Leu Met Val Thr Leu Ser Pro Thr Lys Asp Phe
            180                185                190

Trp Leu His Ala Asn Asn Lys Glu His Ser Val Glu Leu His Lys Cys
        195                200                205

Glu Lys Pro Leu Pro Asp Gln Ala Phe Phe Val Leu His Asn Met His
        210                215                220

Ser Asn Cys Val Ser Phe Glu Cys Lys Thr Asp Pro Gly Val Phe Ile
225                230                235                 240

Gly Val Lys Asp Asn His Leu Ala Leu Ile Lys Val Asp Ser Ser Glu
                245                250                255

Asn Leu Cys Thr Glu Asn Ile Leu Phe Lys Leu Ser Glu Thr
            260                265                270

<210> SEQ ID NO 5
<211> LENGTH: 801
<212> TYPE: DNA
<213> ORGANISM: Mus musculus

<400> SEQUENCE: 5
atgagaccta gaatgaagta ttccaactcc aagatttccc cggcaaagtt cagcagcacc    60
gcaggcgaag ccctggtccc gccttgcaaa ataagaagat cccaacagaa gaccaaagaa   120
ttctgccatg tctactgcat gagactccgt tctggcctca ccataagaaa ggagactagt   180
tattttagga agaacccac gaaaagatat tcactaaaat cgggtaccaa gcatgaagag    240
aacttctctg cctatccacg ggattctagg aagagatcct tgcttggcag tatccaagca   300
tttgctgcgt ctgttgacac attgagcatc caaggaactt cacttttaac acagtctcct   360
gcctccctga gtacatacaa tgaccaatct gttagttttg ttttggagaa tggatgttat   420
gtgatcaatg ttgacgactc tggaaaagac caagagcaag accaggtgct actacgctac   480
tatgagtctc cctgtcctgc aagtcaatca ggcgacggtg tggatgggaa gaaggtgatg   540
gtgaacatga gtcccatcaa agacacagac atcggctgc atgccaacga caaggactac   600
tccgtggagc ttcaaagggg tgacgtctcg cctccggaac aggccttctt cgtccttcac   660
```

```
aaaaagtcct cggactttgt ttcatttgaa tgcaagaatc ttcctggcac ttacatagga    720
gtaaaagata accagctggc tctagtggag gagaaagatg agagctgcaa caatattatg    780
tttaagctct cgaaaatcta a                                              801
```

<210> SEQ ID NO 6
<211> LENGTH: 266
<212> TYPE: PRT
<213> ORGANISM: Mus musculus

<400> SEQUENCE: 6

```
Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
                20                  25                  30

Arg Ser Gln Gln Lys Thr Lys Glu Phe Cys His Val Tyr Cys Met Arg
            35                  40                  45

Leu Arg Ser Gly Leu Thr Ile Arg Lys Glu Thr Ser Tyr Phe Arg Lys
        50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Asp Gly
                165                 170                 175

Lys Lys Val Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
            260                 265
```

<210> SEQ ID NO 7
<211> LENGTH: 801
<212> TYPE: DNA
<213> ORGANISM: Mus musculus

<400> SEQUENCE: 7

```
atgagaccta gaatgaagta ttccaactcc aagatttccc cggcaaagtt cagcagcacc    60
gcaggcgaag ccctggtccc gccttgcaaa ataagaagat cccaacagaa gaccaaagaa   120
ttctgccatg tctactgcat gagactccgt tctggcctca ccataagaaa ggagactagt   180
tattttagga agaacccac gaaaagatat tcactaaaat cgggtaccaa gcatgaagag   240
```

```
aacttctctg cctatccacg ggattctagg aagagatcct tgcttggcag tatccaagca    300
tttgctgcgt ctgttgacac attgagcatc caaggaactt cacttttaac acagtctcct    360
gcctccctga gtacatacaa tgaccaatct gttagttttg ttttggagaa tggatgttat    420
gtgatcaatg ttgacgactc tggaaaagac caagagcaag accaggtgct actacgctac    480
tatgagtctc cctgtcctgc aagtcaatca ggcgacggtg tggctgggaa gaaggtgatg    540
gtgaacatga gtcccatcaa agacacagac atctggctgc atgccaacga caaggactac    600
tccgtggagc ttcaaagggg tgacgtctcg cctccggaac aggccttctt cgtccttcac    660
aaaaagtcct cggactttgt ttcatttgaa tgcaagaatc ttcctggcac ttacatagga    720
gtaaaagata accagctggc tctagtggag gagaaagatg agagctgcaa caatattatg    780
tttaagctct cgaaaatcta a                                              801
```

<210> SEQ ID NO 8
<211> LENGTH: 266
<212> TYPE: PRT
<213> ORGANISM: Mus musculus

<400> SEQUENCE: 8

```
Met Arg Pro Arg Met Lys Tyr Ser Asn Ser Lys Ile Ser Pro Ala Lys
1               5                   10                  15

Phe Ser Ser Thr Ala Gly Glu Ala Leu Val Pro Pro Cys Lys Ile Arg
            20                  25                  30

Arg Ser Gln Gln Lys Thr Lys Glu Phe Cys His Val Tyr Cys Met Arg
        35                  40                  45

Leu Arg Ser Gly Leu Thr Ile Arg Lys Glu Thr Ser Tyr Phe Arg Lys
    50                  55                  60

Glu Pro Thr Lys Arg Tyr Ser Leu Lys Ser Gly Thr Lys His Glu Glu
65                  70                  75                  80

Asn Phe Ser Ala Tyr Pro Arg Asp Ser Arg Lys Arg Ser Leu Leu Gly
                85                  90                  95

Ser Ile Gln Ala Phe Ala Ala Ser Val Asp Thr Leu Ser Ile Gln Gly
            100                 105                 110

Thr Ser Leu Leu Thr Gln Ser Pro Ala Ser Leu Ser Thr Tyr Asn Asp
        115                 120                 125

Gln Ser Val Ser Phe Val Leu Glu Asn Gly Cys Tyr Val Ile Asn Val
    130                 135                 140

Asp Asp Ser Gly Lys Asp Gln Glu Gln Asp Gln Val Leu Leu Arg Tyr
145                 150                 155                 160

Tyr Glu Ser Pro Cys Pro Ala Ser Gln Ser Gly Asp Gly Val Ala Gly
                165                 170                 175

Lys Lys Val Met Val Asn Met Ser Pro Ile Lys Asp Thr Asp Ile Trp
            180                 185                 190

Leu His Ala Asn Asp Lys Asp Tyr Ser Val Glu Leu Gln Arg Gly Asp
        195                 200                 205

Val Ser Pro Pro Glu Gln Ala Phe Phe Val Leu His Lys Lys Ser Ser
    210                 215                 220

Asp Phe Val Ser Phe Glu Cys Lys Asn Leu Pro Gly Thr Tyr Ile Gly
225                 230                 235                 240

Val Lys Asp Asn Gln Leu Ala Leu Val Glu Glu Lys Asp Glu Ser Cys
                245                 250                 255

Asn Asn Ile Met Phe Lys Leu Ser Lys Ile
            260                 265
```

-continued

<210> SEQ ID NO 9
<211> LENGTH: 15
<212> TYPE: PRT
<213> ORGANISM: Homo sapiens

<400> SEQUENCE: 9

Cys Tyr Phe Arg Arg Glu Thr Thr Lys Arg Pro Ser Leu Lys Thr
1               5                   10                  15

<210> SEQ ID NO 10
<211> LENGTH: 4
<212> TYPE: PRT
<213> ORGANISM: Homo sapiens

<400> SEQUENCE: 10

Asp Gly Val Asp
1

<210> SEQ ID NO 11
<211> LENGTH: 4
<212> TYPE: PRT
<213> ORGANISM: Mus musculus

<400> SEQUENCE: 11

Asp Gly Val Asp
1

<210> SEQ ID NO 12
<211> LENGTH: 178
<212> TYPE: PRT
<213> ORGANISM: Homo sapiens

<400> SEQUENCE: 12

Met Lys Pro Lys Met Lys Tyr Ser Thr Asn Lys Ile Ser Thr Ala Lys
1               5                   10                  15

Trp Lys Asn Thr Ala Ser Lys Ala Leu Cys Phe Lys Leu Gly Lys Ser
            20                  25                  30

Gln Gln Lys Ala Lys Gly Val Cys Pro Met Tyr Phe Met Lys Leu Arg
        35                  40                  45

Ser Gly Leu Met Ile Lys Lys Glu Ala Cys Tyr Phe Arg Arg Gly Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
            100                 105                 110

Ile Thr Gly Ile Ser Pro Ile Thr Glu Tyr Leu Ala Ser Leu Ser Thr
        115                 120                 125

Tyr Asn Asp Gln Ser Ile Thr Phe Ala Leu Glu Asp Glu Ser Tyr Glu
    130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp

<210> SEQ ID NO 13
<211> LENGTH: 92
<212> TYPE: PRT

<213> ORGANISM: Homo sapiens

<400> SEQUENCE: 13

Gly Lys Met Leu Met Val Thr Leu Ser Pro Thr Lys Asp Phe Trp Leu
1               5                   10                  15

His Ala Asn Asn Lys Glu His Ser Val Glu Leu His Lys Cys Glu Lys
            20                  25                  30

Pro Leu Pro Asp Gln Ala Phe Phe Val Leu His Asn Met His Ser Asn
        35                  40                  45

Cys Val Ser Phe Glu Cys Lys Thr Asp Pro Gly Val Phe Ile Gly Val
    50                  55                  60

Lys Asp Asn His Leu Ala Leu Ile Lys Val Asp Ser Ser Glu Asn Leu
65                  70                  75                  80

Cys Thr Glu Asn Ile Leu Phe Lys Leu Ser Glu Thr
                85                  90

<210> SEQ ID NO 14
<211> LENGTH: 159
<212> TYPE: PRT
<213> ORGANISM: Homo sapiens

<400> SEQUENCE: 14

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

Gly Val Asp Gly Lys Met Leu Met Val Thr Leu Ser Pro Thr Lys Asp
65                  70                  75                  80

Phe Trp Leu His Ala Asn Asn Lys Glu His Ser Val Glu Leu His Lys
                85                  90                  95

Cys Glu Lys Pro Leu Pro Asp Gln Ala Phe Phe Val Leu His Asn Met
            100                 105                 110

His Ser Asn Cys Val Ser Phe Glu Cys Lys Thr Asp Pro Gly Val Phe
        115                 120                 125

Ile Gly Val Lys Asp Asn His Leu Ala Leu Ile Lys Val Asp Ser Ser
    130                 135                 140

Glu Asn Leu Cys Thr Glu Asn Ile Leu Phe Lys Leu Ser Glu Thr
145                 150                 155

<210> SEQ ID NO 15
<211> LENGTH: 67
<212> TYPE: PRT
<213> ORGANISM: Homo sapiens

<400> SEQUENCE: 15

Ser Ile Thr Gly Ile Ser Pro Ile Thr Glu Tyr Leu Ala Ser Leu Ser
1               5                   10                  15

Thr Tyr Asn Asp Gln Ser Ile Thr Phe Ala Leu Glu Asp Glu Ser Tyr
            20                  25                  30

Glu Ile Tyr Val Glu Asp Leu Lys Lys Asp Glu Lys Lys Asp Lys Val
        35                  40                  45

Leu Leu Ser Tyr Tyr Glu Ser Gln His Pro Ser Asn Glu Ser Gly Asp
    50                  55                  60

```
Gly Val Asp
 65

<210> SEQ ID NO 16
<211> LENGTH: 44
<212> TYPE: PRT
<213> ORGANISM: Homo sapiens

<400> SEQUENCE: 16

Lys Lys Asp Lys Val Leu Leu Ser Tyr Tyr Glu Ser Gln His Pro Ser
  1               5                  10                  15

Asn Glu Ser Gly Asp Gly Val Asp Gly Lys Met Leu Met Val Thr Leu
             20                  25                  30

Ser Pro Thr Lys Asp Phe Trp Leu His Ala Asn Asn
         35                  40

<210> SEQ ID NO 17
<211> LENGTH: 24
<212> TYPE: PRT
<213> ORGANISM: Homo sapiens

<400> SEQUENCE: 17

Glu Ser Gln His Pro Ser Asn Glu Ser Gly Asp Gly Val Asp Gly Lys
  1               5                  10                  15

Met Leu Met Val Thr Leu Ser Pro
             20
```